United States Patent
Kuniyoshi et al.

(10) Patent No.: US 12,202,850 B2
(45) Date of Patent: Jan. 21, 2025

(54) CYCLOBUTYL PURINE DERIVATIVE OR SALT THEREOF

(71) Applicant: FUJIFILM Corporation, Tokyo (JP)

(72) Inventors: Hidenobu Kuniyoshi, Kanagawa (JP);
Takehiro Yamane, Kanagawa (JP);
Takayuki Yamakawa, Kanagawa (JP);
Shintaro Tanabe, Kanagawa (JP);
Hideyasu Fujiwara, Kanagawa (JP);
Eiichi Kodama, Sendai (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/296,151

(22) Filed: Apr. 5, 2023

(65) Prior Publication Data
US 2023/0295202 A1    Sep. 21, 2023

Related U.S. Application Data

(60) Division of application No. 17/158,520, filed on Jan. 26, 2021, now abandoned, which is a continuation of application No. PCT/JP2019/029448, filed on Jul. 26, 2019.

(30) Foreign Application Priority Data

Jul. 27, 2018 (JP) .................. 2018-141749

(51) Int. Cl.
*A61K 31/683* (2006.01)
*A61P 31/20* (2006.01)
*C07F 9/6561* (2006.01)

(52) U.S. Cl.
CPC ........ *C07F 9/65616* (2013.01); *A61K 31/683* (2013.01); *A61P 31/20* (2018.01)

(58) Field of Classification Search
CPC .................................................. A61K 31/683
See application file for complete search history.

(56) References Cited

U.S. PATENT DOCUMENTS

| | | |
|---|---|---|
| 5,034,394 A | 7/1991 | Daluge |
| 5,324,730 A | 6/1994 | Ichikawa et al. |
| 5,369,098 A | 11/1994 | Slusarchyk |
| 2001/0031745 A1 | 10/2001 | McGuigan et al. |
| 2004/0167096 A1 | 8/2004 | Cheng et al. |
| 2021/0147456 A1 | 5/2021 | Kuniyoshi et al. |
| 2023/0295202 A1 | 9/2023 | Kuniyoshi et al. |

FOREIGN PATENT DOCUMENTS

| | | |
|---|---|---|
| CA | 1339896 C | 6/1998 |
| CN | 1328565 A | 12/2001 |
| JP | 2-45486 A | 2/1990 |
| JP | H02-131473 A | 5/1990 |
| JP | 4-91094 A | 3/1992 |
| JP | 4-297463 A | 10/1992 |
| JP | 2793825 B2 | 9/1998 |
| JP | 2002-525374 A | 8/2002 |
| WO | 93/00099 A2 | 1/1993 |
| WO | 01/42256 A1 | 6/2001 |

OTHER PUBLICATIONS

Amy E. Caruso Brown et al., "Pharmacokinetics and Safety of Intravenous Cidofovir for Life-Threatening Viral Infections in Pediatric Hematopoietic Stem Cell Transplant Recipients", Antimicrobial Agents and Chemotherapy, Jul. 2015, vol. 59, No. 7, pp. 3718-3725 (8 pages).
Chrysanthi L. Skevaki et al., "Treatment of Viral Conjunctivitis with Antiviral Drugs", Drugs, 2011, vol. 71, No. 3, pp. 331-347 (17 pages).
L. Lenaerts et al., "Antiviral therapy for adenovirus infections", Antiviral Research, 2006, vol. 71, pp. 172-180 (10 pages).
Office Action dated Jun. 14, 2022 from the European Patent Office in Application No. 19842018.4.
Office Action issued Jan. 18, 2022 in Japanese Application No. 2020-532503.
Peter C Van Der Vliet et al., "Role of DNA polymerase γ in adenovirus DNA replication, Mechanism of inhibition by 2', 3'-Dideoxynucleoside 5'-Triphosphates", 1981, Biochemistry, vol. 20, pp. 2628-2632 (5 pages total).
Toyofumi Yamaguchi et al., "Synthetic Nucleosides and Nucleotides. 43. Inhibition of Vertebrate Telomerases by Carbocyclic Oxetanocin G (C.OXT-G) Triphosphate Analogues and Influence of C.OXT-G Treatment on Telomere Length in Human HL60 Cells", Nucleosides, Nucleotides, and Nucleic Acids, 2006, vol. 25, pp. 539-551 (13 pages).

(Continued)

*Primary Examiner* — David K O'Dell
(74) *Attorney, Agent, or Firm* — Sughrue Mion, PLLC

(57) ABSTRACT

An object of the present invention is to provide a compound exhibiting an excellent drug efficacy as an anti-adenoviral agent, and an anti-adenoviral agent. The present invention provides a compound represented by General Formula [1]

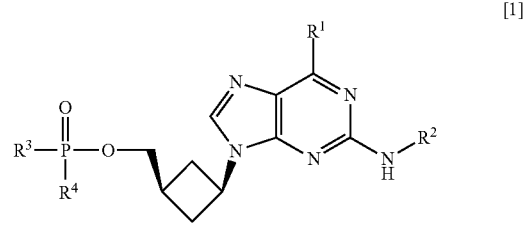

[1]

(in the formula, $R^1$ represents a halogen atom, an amino group which may be substituted, a $C_{1-6}$ alkoxy group which may be substituted, a hydroxyl group which may be protected, or the like; $R^2$ represents a hydrogen atom or an amino protecting group; $R^3$ represents a $C_{1-20}$ alkoxy group which may be substituted, an aryloxy group which may be substituted, an amino group which may be substituted, or the like; $R^4$ represents a $C_{1-20}$ alkoxy group which may be substituted, an aryloxy group which may be substituted, an amino group which may be substituted, or the like); or a salt thereof.

10 Claims, 1 Drawing Sheet
Specification includes a Sequence Listing.

(56) References Cited

OTHER PUBLICATIONS

International Preliminary Report on Patentability dated Feb. 2, 2021, issued by the International Searching Authority in application No. PCT/JP2019/029448.

International Search Report dated Oct. 1, 2019, issued by the International Searching Authority in application No. PCT/JP2019/029448.

Toyofumi Yamaguchi et al., "Synthetic Nucleosides and Nucleotides. 43. Inhibition of Vertebrate Telomerases by Carbocyclic Oxetanocin G (C.OXT-G) Triphosphate Analgues" and Influence of C.OXT-G Treatment on Telomere Length in Human HL60 Cells, Nucleotides & Nucleic Acids, vol. 25, No. 4-6, Jan. 1, 2006, XP055666350, pp. 539-551, ( 14 pages total).

Abstract of Toyofumi Yamaguchi et al., "Synthetic Nucleosides and Nucleotides. 43. Inhibition of Vertebrate Telomerases by Carbocyclic Oxetanocin G (C.OXT-G) Triphosphate Analogues and Influence of C.OXT-G Treatment on Telomere Length in Human HL60 Cells", Nucleosides, Nucleotides & Nucleic Acids, vol. 25, No. 4-6, Jan. 1, 2006, pp. 539-551, provided by Reaxys, a trademark of Elsevier Life Sciences IP Limited (2 pages total).

Written Opinion dated Oct. 1, 2019, issued by the International Searching Authority in application No. PCT/JP2019/029448.

Mehellou, "Aryloxy Phosphoramidate Triesters: a Technology for Delivering Monophosphorylated Nucleosides and Sugars into Cells" ChemMedChem (2009), 4(11), 1779-1791.

Roman "Diastereoselective Synthesis of (Aryloxy)phosphoramidate Prodrugs," Arbelo, Cristina; European Journal of Organic Chemistry, 2011 (25), 4899-4909.

Mehellou, "The ProTide Prodrug Technology: From the Concept to the Clinic," Journal of Medicinal Chemistry (2018), 61(6), 2211-22.

Sinokrot, "Advanced prodrug strategies in nucleoside and non-nucleoside antiviral agents: a review of the recent five years," Molecules (2017), 22(10), 1736/1-1736/18.

Wang, "Phosphoramidate prodrugs of (−)-3-D-(2R,4R)-dioxolane-thymine (DOT) as potent anti-HIV agents," Antiviral Chemistry & Chemotherapy, 2012, 22(5), 217-238.

McGuigan, "The application of phosphoramidate ProTide technology to the potent anti-HCV compound 4'-azidocytidine (R1479)," Bioorganic & Medicinal Chemistry Letters, 2009, 19(15), 4250-4254.

Extended European Search Report dated Aug. 19, 2021, from the European Patent Office in European application No. 19842018.4.

Communication dated Dec. 8, 2023, issued in Chinese Application No. 201980050210.2, corresponding to U.S. Appl. No. 17/158,547.

Office Action dated Jun. 28, 2023 in Chinese Application No. 201980050210.2 corresponding to U.S. Appl. No. 17/158,547.

Communication dated May 20, 2022, issued in European Application No. 19 840 531.8, corresponding to U.S. Appl. No. 17/158,547.

Office Action dated Dec. 7, 2021 from the Japanese Patent Office in Japanese Application No. 2020-532502, corresponding to U.S. Appl. No. 17/158,547.

International Search Report dated Sep. 10, 2019 from the International Searching Authority in International Application No. PCT/JP2019/029447, corresponding to U.S. Appl. No. 17/158,547.

Written Opinion dated Sep. 10, 2019 from the International Bureau in International Application No. PCT/JP2019/029447, corresponding to U.S. Appl. No. 17/158,547.

International Preliminary Report on Patentability dated Feb. 2, 2021 from the International Bureau in International Application No. PCT/JP2019/029447, corresponding to U.S. Appl. No. 17/158,547.

Office Action issued Aug. 25, 2022 in U.S. Appl. No. 17/158,520.

Office Action issued Jan. 5, 2023 in U.S. Appl. No. 17/158,520.

Office Action issued Mar. 7, 2024 in U.S. Appl. No. 17/158,547.

Extended European Search Report dated Aug. 2, 2021 from the European Patent Office in European Application No. 19840531.8, corresponding to U.S. Appl. No. 17/158,547.

R. Anthony Vere Hodge, "Meeting report: 29th International Conference on Antiviral Research in La Jolla, CA, USA", Antiviral Research, 2017, vol. 137, pp. 23-40 (18 pages total).

McGuigan et al., "Application of Phosphoramidate Pronucleotide Technology to Abacavir Leads to a significant Enhancement of Antiviral Potency", J. Med. Chem., 2005, vol. 48, No. 10, 3504-3515.

Uchio et al., "Anti-adenoviral effect of anti-HIV agents in vitro in serotypes inducing keratoconjunctivitis", Graefe's Arch Clin Exp Ophthalmol, 2007, vol. 245, 1319-1325.

Office Action issued Jul. 31, 2024 in U.S. Appl. No. 17/158,547.

Notice of Allowance issued Nov. 6, 2024 in U.S. Appl. No. 17/158,547.

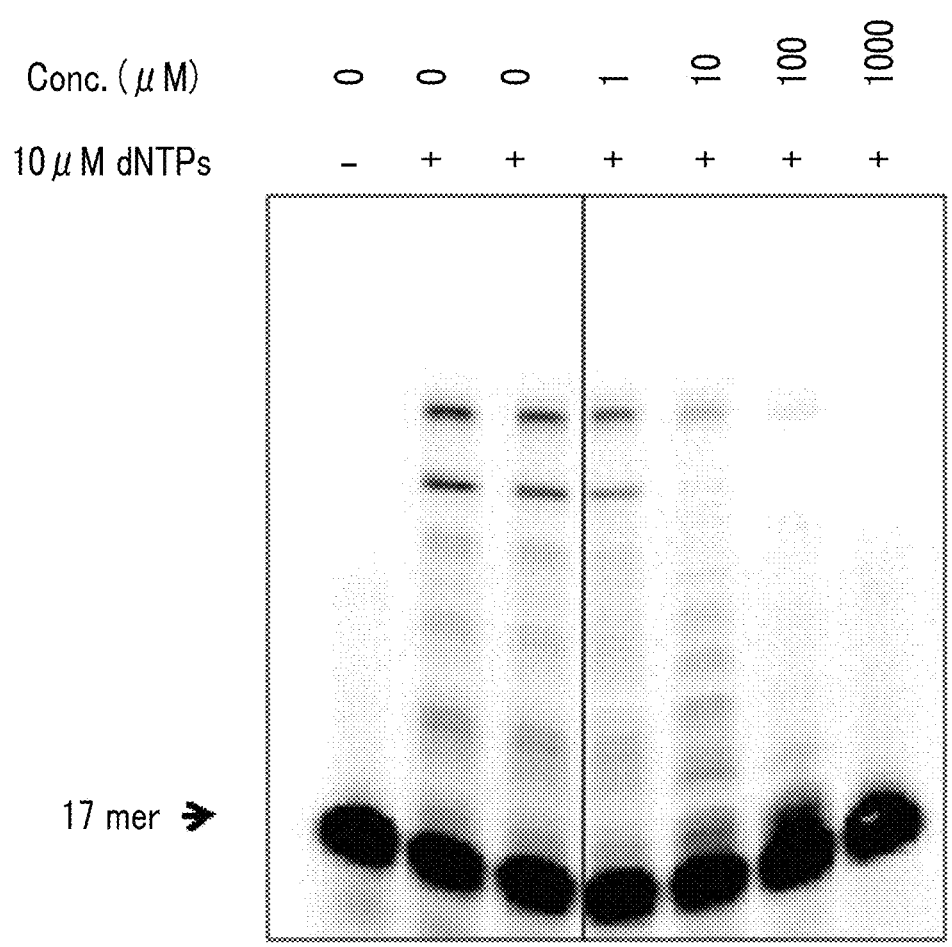

CYCLOBUTYL PURINE DERIVATIVE OR SALT THEREOF

CROSS-REFERENCE TO RELATED APPLICATIONS

This application is a Divisional of application Ser. No. 17/158,520 filed Jan. 26, 2021, which is a Continuation of PCT International Application No. PCT/JP2019/029448 filed on Jul. 26, 2019, which claims priority under 35 U.S.C § 119(a) to Japanese Patent Application No. 2018-141749 filed on Jul. 27, 2018. Each of the above application(s) is hereby expressly incorporated by reference, in its entirety, into the present application.

INCORPORATION BY REFERENCE OF SEQUENCE LISTING

The content of the electronically submitted sequence listing, file name: Q285873_Sequence listing as filed.xml; size: 3.43 kilobytes; and date of creation: Apr. 3, 2023, filed herewith, is incorporated herein by reference in its entirety.

BACKGROUND OF THE INVENTION

1. Field of the Invention

The present invention relates to a cyclobutyl purine derivative or a salt thereof and an anti-adenoviral agent containing the same.

2. Description of the Related Art

Adenovirus is a double-stranded linear DNA virus and is a causative virus that causes various pathological conditions such as respiratory infection, pharyngoconjunctival fever, epidemic keratoconjunctivitis, hepatitis, gastroenteritis, cystitis, and encephalitis.

Although there is no pharmaceutical product approved as an anti-adenoviral agent, for example, cidofovir is known to be clinically effective (Antiviral Research, vol. 71, pp. 172 to 180, 2006). On the other hand, cidofovir is known to be toxic upon systemic administration and ocular instillation administration (Antimicrobial Agents and Chemotherapy, vol. 59 (7), pp. 3718 to 3725, 2015, and Drugs, vol. 71 (3), pp. 331 to 347, 2011).

On the other hand, cyclobutyl purine derivatives are expected to be applied to various pharmaceutical products, and for example, compounds having an anti-herpesvirus effect and an anti-human immunodeficiency virus activity are known (JP1990-131473A (JP-H02-131473A)).

SUMMARY OF THE INVENTION

An object of the present invention is to provide a compound exhibiting an excellent drug efficacy against adenovirus and an excellent anti-adenoviral agent.

As a result of extensive studies, the present inventors have found that a compound represented by General Formula [1] or a salt thereof exhibits an excellent drug efficacy against adenovirus. The present invention has been completed based on these findings.

The present invention provides the following.

(1) A compound represented by General Formula [1]:

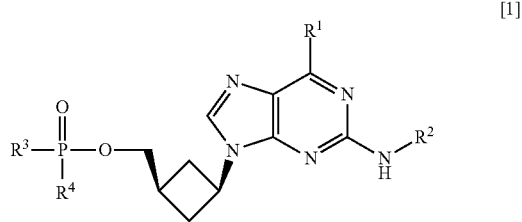

in the formula, $R^1$ represents a halogen atom, an amino group which may be substituted, a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected;

$R^2$ represents a hydrogen atom or an amino protecting group;

$R^3$ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or —O—P(O)(OH)—O—PO$_3$H; and $R^4$ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or a hydroxyl group which may be protected; or $R^3$ and $R^4$, together with a phosphorus atom to which $R^3$ and $R^4$ are bonded, may be combined to form a 5- to 10-membered nitrogen- and phosphorus-containing heterocyclic ring which may be substituted, a 5- to 10-membered oxygen- and phosphorus-containing heterocyclic ring which may be substituted, or a 5- to 10-membered nitrogen-, oxygen-, and phosphorus-containing heterocyclic ring which may be substituted, provided that $R^2$ represents a hydrogen atom in a case where $R^3$ represents —O—P(O)(OH)—O—PO$_3$H; or a salt thereof.

(2) The compound according to (1), in which $R^2$ is a hydrogen atom; or the salt thereof.

(3) The compound according to (1) or (2), in which $R^1$ is a halogen atom, an amino group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylthio group which may be substituted with one or more substituents selected from Substituent group A, a hydroxyl group which may be protected, or a thiol group which may be protected; or the salt thereof.

Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; a $C_{1-6}$ alkoxycarbonyloxy group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an ar-$C_{1-6}$ alkoxycarbonyl group; an aryl group; an aryloxy group; a heterocyclic oxy group which may be substituted with one or more substituents selected from a hydroxyl group and a hydroxymethyl group; an ar-$C_{1-6}$ alkoxy group; and an acyloxy group.

(4) The compound according to (3), in which $R^1$ is a halogen atom, an amino group which may be substituted with one or more substituents selected from Substituent group A, a $C_{1-6}$ alkoxy group which may be substituted with one or more substituents selected from Substituent group A, a hydroxyl group which may be protected, or a thiol group which may be protected; or the salt thereof.

(5) The compound according to (3), in which $R^1$ is a halogen atom, an amino group which may be substituted with one or more substituents selected from Substituent group A, a $C_{1-6}$ alkoxy group which may be substituted with one or more substituents selected from Substituent group A, or a hydroxyl group; or the salt thereof.

(6) The compound according to any one of (1) to (5), in which $R^3$ is a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or —O—P(O)(OH)—O—PO$_3$H; or the salt thereof.

Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; a $C_{1-6}$ alkoxycarbonyloxy group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an ar-$C_{1-6}$ alkoxycarbonyl group; an aryl group; an aryloxy group; a heterocyclic oxy group which may be substituted with one or more substituents selected from a hydroxyl group and a hydroxymethyl group; an ar-$C_{1-6}$ alkoxy group; and an acyloxy group.

(7) The compound according to (6), in which $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or —O—P(O)(OH)—O—PO₃H; or the salt thereof.

(8) The compound according to (6), in which $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, or —O—P(O)(OH)—O—PO₃H; or the salt thereof.

(9) The compound according to any one of (1) to (8), in which $R^4$ is a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or a hydroxyl group which may be protected; or the salt thereof.

Substituent group A:
a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; a $C_{1-6}$ alkoxycarbonyloxy group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

Substituent group B:
a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an ar-$C_{1-6}$ alkoxycarbonyl group; an aryl group; an aryloxy group; a heterocyclic oxy group which may be substituted with one or more substituents selected from a hydroxyl group and a hydroxymethyl group; an ar-$C_{1-6}$ alkoxy group; and an acyloxy group.

(10) The compound according to (9), in which $R^4$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected; or the salt thereof.

(11) The compound according to (9), in which $R^4$ is a $C_{1-20}$ alkoxy group which may be substituted with one or more substituents selected from Substituent group A, an amino group which may be substituted with one or more substituents selected from Substituent group A, or a hydroxyl group which may be protected; or the salt thereof.

(12) The compound according to any one of (1) to (5), in which a ring formed by combining $R^3$ and $R^4$ together with a phosphorus atom to which $R^3$ and $R^4$ are bonded is a 5- to 10-membered oxygen- and phosphorus-containing heterocyclic ring which may be substituted; or the salt thereof.

(13) A compound selected from methyl (((cis-3-(2-amino-6-methoxy-9H-purin-9-yl)cyclobutyl)methoxy)(phenoxy)phosphoryl)-L-alaninate, methyl (((cis-3-(2-amino-6-methoxy-9H-purin-9-yl)cyclobutyl)methoxy)(naphthalen-1-yloxy)phosphoryl)-L-alaninate, methyl (((cis-3-(2-amino-6-methoxy-9H-purin-9-yl)cyclobutyl)methoxy)(4-chlorophenoxy)phosphoryl)-L-alaninate, methyl (((cis-3-(2-amino-6-methoxy-9H-purin-9-yl)cyclobutyl)methoxy)(4-bromophenoxy)phosphoryl)-L-alaninate, ethyl (((cis-3-(2-amino-6-methoxy-9H-purin-9-yl)cyclobutyl)methoxy)(4-bromophenoxy)phosphoryl)-L-alaninate, ethyl (((cis-3-(2-amino-6-methoxy-9H-purin-9-yl)cyclobutyl)methoxy)(4-chlorophenoxy)phosphor yl)-L-alaninate, methyl (((cis-3-(2-amino-6-methoxy-9H-purin-9-yl)cyclobutyl)methoxy)(2-bromophenoxy)phosphoryl)-L-alaninate, methyl (((cis-3-(2-amino-6-methoxy-9H-purin-9-yl)cyclobutyl)methoxy)(2-chlorophenoxy)phosphoryl)-L-alaninate, methyl (((cis-3-(2-amino-6-methoxy-9H-purin-9-yl)cyclobutyl)methoxy)(2-(pivaloylthio)ethoxy)phosphoryl)-L-alaninate, methyl (((cis-3-(2-amino-6-ethoxy-9H-purin-9-yl)cyclobutyl)methoxy)(4-bromophenoxy)phosphoryl)-L-alaninate, methyl 2-((((cis-3-(2-amino-6-methoxy-9H-purin-9-yl)cyclobutyl)methoxy)(4-bromophenoxy)phosphoryl)amino)-2-methylpropanoate, (cis-3-(2-amino-6-methoxy-9H-purin-9-yl)cyclobutyl)methyl bis(pivaloyloxymethyl)phosphate, methyl (((cis-3-(2-amino-6-methoxy-9H-purin-9-yl)cyclobutyl)methoxy)(4-chloro-2-fluorophenoxy) phosphoryl)-L-alaninate, and methyl (((cis-3-(2-amino-6-methoxy-9H-purin-9-yl)cyclobutyl)methoxy)(3-bromophenoxy)phosphoryl)-L-alaninate; or a salt thereof.

(14) An anti-adenoviral agent comprising:
the compound or salt thereof according to any one of (1) to (13).
(A) A medicine for treating an adenovirus infection, comprising:
the compound or salt thereof according to any one of (1) to (13).
(B) A method for suppressing adenovirus, comprising:
administering the compound or salt thereof according to any one of (1) to (13) to a subject (preferably a mammal such as a human).
(C) A method for treating an adenovirus infection, comprising:
administering the compound or salt thereof according to any one of (1) to (13) to a subject (preferably a mammal such as a human).
(D) The compound or salt thereof according to any one of (1) to (13), for use in suppressing adenovirus.
(E) The compound or salt thereof according to any one of (1) to (13), for use in the treatment of an adenovirus infection.
(F) Use of the compound or salt thereof according to any one of (1) to (13) for the production of an anti-adenoviral agent.
(G) Use of the compound or salt thereof according to any one of (1) to (13) for the production of a medicine for treating an adenovirus infection.

The compound represented by General Formula [1] or a salt thereof according to an aspect of the present invention is useful as an anti-adenoviral agent. The compound represented by General Formula [1] or a salt thereof according to the aspect of the present invention is useful as an agent for treating adenovirus.

BRIEF DESCRIPTION OF THE DRAWINGS

FIG. 1 shows the results of electrophoresis. An extension reaction of DNA was evaluated by detecting a fluorescently labeled DNA.

DESCRIPTION OF THE PREFERRED EMBODIMENTS

Hereinafter, the present invention will be described in detail.

In the present invention, the individual terms have the following meanings, unless otherwise indicated.

The halogen atom refers to a fluorine atom, a chlorine atom, a bromine atom, or an iodine atom.

The $C_{1-6}$ alkyl group refers to a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, or a hexyl group.

The $C_{1-20}$ alkyl group refers to a linear or branched $C_{1-20}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a heptyl group, a 1-methylhexyl group, a 2-methylhexyl group, a 3-methylhexyl group, a 4-methylhexyl group, a 5-methylhexyl group, a 1-propylbutyl group, a 4,4-dimethylpentyl group, an octyl group, a 1-methylheptyl group, a 2-methylheptyl group, a 3-methylheptyl group, a 4-methylheptyl group, a 5-methylheptyl group, a 6-methylheptyl group, a 1-propylpentyl group, a 2-ethylhexyl group, a 5,5-dimethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, or an eicosanyl group.

The $C_{1-6}$ alkylthio group refers to a linear or branched $C_{1-6}$ alkylthio group such as a methylthio group, an ethylthio group, a propylthio group, an isopropylthio group, a butylthio group, an isobutylthio group, a sec-butylthio group, a tert-butylthio group, a pentylthio group, or a hexylthio group.

The $C_{1-20}$ alkylthio group refers to a linear or branched $C_{1-20}$ alkylthio group such as a methylthio group, an ethylthio group, a propylthio group, an isopropylthio group, a butylthio group, an isobutylthio group, a sec-butylthio group, a tert-butylthio group, a pentylthio group, a hexylthio group, a heptylthio group, an octylthio group, a nonylthio group, a decylthio group, an undecylthio group, a dodecylthio group, a tridecylthio group, a tetradecylthio group, a pentadecylthio group, a hexadecylthio group, a heptadecylthio group, an octadecylthio, a nonadecylthio group, or an eicosanylthio group.

The $C_{1-6}$ alkylsulfonyl group refers to a $C_{1-6}$ alkylsulfonyl group such as a methylsulfonyl group, an ethylsulfonyl group, or a propylsulfonyl group.

The $C_{1-6}$ alkylsulfonyloxy group refers to a $C_{1-6}$ alkylsulfonyloxy group such as a methylsulfonyloxy group or an ethylsulfonyloxy group.

The $C_{1-6}$ alkyldisulfanyl group refers to a linear or branched $C_{1-6}$ alkyldisulfanyl group such as a methyldisulfanyl group, an ethyldisulfanyl group, a propyldisulfanyl group, an isopropyldisulfanyl group, a butyldisulfanyl group, a sec-butyldisulfanyl group, an isobutyldisulfanyl group, a tert-butyldisulfanyl group, a pentyldisulfanyl group, an isopentyldisulfanyl group, a 2-methylbutyldisulfanyl group, a 2-pentyldisulfanyl group, a 3-pentyldisulfanyl group, or a hexyldisulfanyl group.

The $C_{2-6}$ alkenyl group refers to a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

The $C_{2-6}$ alkynyl group refers to a linear or branched $C_{2-6}$ alkynyl group such as an ethynyl group, a propynyl group, a butynyl group, a pentynyl group, or a hexynyl group.

The $C_{3-8}$ cycloalkyl group refers to a $C_{3-8}$ cycloalkyl group such as a cyclopropyl group, a cyclobutyl group, a cyclopentyl group, a cyclohexyl group, or a cycloheptyl group.

The $C_{3-8}$ cycloalkyldisulfanyl group refers to a $C_{3-8}$ cycloalkyldisulfanyl group such as a cyclopropyldisulfanyl group, a cyclobutyldisulfanyl group, cyclopentyldisulfanyl group, a cyclohexyldisulfanyl group, or a cycloheptyldisulfanyl group.

The $C_{1-6}$ alkoxy group refers to a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group, or a hexyloxy group.

The $C_{1-20}$ alkoxy group refers to a linear or branched $C_{1-20}$ alkyloxy group such as a methoxy group, an ethoxy group, a propoxy group, an isopropoxy group, a butoxy group, an isobutoxy group, a sec-butoxy group, a tert-butoxy group, a pentyloxy group, a hexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, or an eicosanyloxy group.

The $C_{1-6}$ alkoxy $C_{1-6}$ alkyl group refers to a $C_{1-6}$ alkyloxy $C_{1-6}$ alkyl group such as a methoxymethyl group or a 1-ethoxyethyl group.

The $C_{1-6}$ alkoxycarbonyl group refers to a linear or branched $C_{1-6}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, or a hexyloxycarbonyl group.

The $C_{1-20}$ alkoxycarbonyl group refers to a linear or branched $C_{1-20}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a hexyloxycarbonyl group, a heptyloxycarbonyl group, an octyloxycarbonyl group, a nonyloxycarbonyl group, a decyloxycarbonyl group, an undecyloxycarbonyl group, a dodecyloxycarbonyl group, a tridecyloxycarbonyl group, a tetradecyloxycarbonyl group, a pentadecyloxycarbonyl group, a hexadecyloxycarbonyl group, a heptadecyloxycarbonyl group, an octadecyloxycarbonyl group, a nonadecyloxycarbonyl group, or an eicosanyloxycarbonyl group.

The $C_{1-6}$ alkoxycarbonyloxy group refers to a linear or branched $C_{1-6}$ alkyloxycarbonyloxy group such as a methoxycarbonyloxy group, an ethoxycarbonyloxy group, a propoxycarbonyloxy group, an isopropoxycarbonyloxy group, a butoxycarbonyloxy group, an isobutoxycarbonyloxy group, a sec-butoxycarbonyloxy group, a tert-butoxycarbonyloxy group, a pentyloxycarbonyloxy group, or a hexyloxycarbonyloxy group.

The $C_{3-8}$ cycloalkoxy group refers to a $C_{3-8}$ cycloalkyloxy group such as a cyclopropoxy group, a cyclobutoxy group, a cyclopentyloxy group, a cyclohexyloxy group, or a cycloheptyloxy group.

The $C_{3-8}$ cycloalkoxycarbonyl group refers to a $C_{3-8}$ cycloalkoxycarbonyl group such as a cyclopropoxycarbonyl group, a cyclobutoxycarbonyl group, a cyclopentyloxycarbonyl group, a cyclohexyloxycarbonyl group, a cycloheptyloxycarbonyl group, or a cyclooctyloxycarbonyl group.

The aryl group refers to a phenyl group or a naphthyl group.

The aryloxy group refers to a phenoxy group, a naphthalen-1-yloxy group, or a naphthalen-2-yloxy group.

The arylsulfonyl group refers to a benzenesulfonyl group, a p-toluenesulfonyl group, or a naphthalenesulfonyl group.

The arylsulfonyloxy group refers to a benzenesulfonyloxy group or a p-toluenesulfonyloxy group.

The aryldisulfanyl group refers to a phenyldisulfanyl group or a naphthyldisulfanyl group.

The ar-$C_{1-6}$ alkyl group refers to an ar-$C_{1-6}$ alkyl group such as a benzyl group, a diphenylmethyl group, a trityl group, a phenethyl group, a 2-phenylpropyl group, a 3-phenylpropyl group, or a naphthylmethyl group.

The ar-$C_{1-6}$ alkoxy group refers to an ar-$C_{1-6}$ alkyloxy group such as a benzyloxy group, a diphenylmethoxy group, a trityloxy group, a phenethyloxy group, a 2-phenylpropoxy group, a 3-phenylpropoxy group, or a naphthylmethoxy group.

The ar-$C_{1-6}$ alkoxy $C_{1-6}$ alkyl group refers to an ar-$C_{1-6}$ alkyloxy $C_{1-6}$ alkyl group such as a benzyloxymethyl group or a phenethyloxymethyl group.

The ar-$C_{1-6}$ alkoxycarbonyl group refers to an ar-$C_{1-6}$ alkyloxycarbonyl group such as a benzyloxycarbonyl group or a phenethyloxycarbonyl group.

The monocyclic nitrogen-containing heterocyclic ring group refers to a monocyclic nitrogen-containing heterocyclic ring group which contains only a nitrogen atom as a heteroatom forming the ring, such as an aziridinyl group, an azetidinyl group, a pyrrolidinyl group, a pyrrolinyl group, a pyrrolyl group, a piperidyl group, a tetrahydropyridyl group, a dihydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, or a tetrazolyl group.

The monocyclic oxygen-containing heterocyclic ring group refers to a monocyclic oxygen-containing heterocyclic ring group which contains only an oxygen atom as a heteroatom forming the ring, such as an oxetanyl group, a tetrahydrofuranyl group, a furanyl group, a tetrahydropyranyl group, a pyranyl group, a 1,3-dioxanyl group, or a 1,4-dioxanyl group.

The monocyclic sulfur-containing heterocyclic ring group refers to a thienyl group.

The monocyclic nitrogen- and oxygen-containing heterocyclic ring group refers to a monocyclic nitrogen- and oxygen-containing heterocyclic ring group which contains only a nitrogen atom and an oxygen atom as heteroatoms forming the ring, such as an oxazolyl group, an isoxazolyl group, an oxadiazolyl group, a morpholinyl group, or an oxazepanyl group.

The monocyclic nitrogen- and sulfur-containing heterocyclic ring group refers to a monocyclic nitrogen- and sulfur-containing heterocyclic ring group which contains only a nitrogen atom and a sulfur atom as heteroatoms forming the ring, such as a thiazolyl group, an isothiazolyl group, a thiadiazolyl group, a thiomorpholinyl group, a 1-oxidothiomorpholinyl group, or a 1,1-dioxidothiomorpholinyl group.

The monocyclic heterocyclic ring group refers to a monocyclic nitrogen-containing heterocyclic ring group, a monocyclic oxygen-containing heterocyclic ring group, a monocyclic sulfur-containing heterocyclic ring group, a monocyclic nitrogen- and oxygen-containing heterocyclic ring group, or a monocyclic nitrogen- and sulfur-containing heterocyclic ring group.

The bicyclic nitrogen-containing heterocyclic ring group refers to a bicyclic nitrogen-containing heterocyclic ring group which contains only a nitrogen atom as a heteroatom forming the ring, such as an indolinyl group, an indolyl group, an isoindolinyl group, an isoindolyl group, a benzimidazolyl group, an indazolyl group, a benzotriazolyl group, a pyrazolopyridinyl group, a quinolyl group, a tetrahydroquinolinyl group, a quinolyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group, or a quinuclidinyl group.

The bicyclic oxygen-containing heterocyclic ring group refers to a bicyclic oxygen-containing heterocyclic ring group which contains only an oxygen atom as a heteroatom forming the ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

The bicyclic sulfur-containing heterocyclic ring group refers to a bicyclic sulfur-containing heterocyclic ring group which contains only a sulfur atom as a heteroatom forming the ring, such as a 2,3-dihydrobenzothienyl group or a benzothienyl group.

The bicyclic nitrogen- and oxygen-containing heterocyclic ring group refers to a bicyclic nitrogen- and oxygen-containing heterocyclic ring group which contains only a nitrogen atom and an oxygen atom as heteroatoms forming the ring, such as a benzoxazolyl group, a benzisoxazolyl group, a benzoxadiazolyl group, a benzomorpholinyl group, a dihydropyranopyridyl group, a dioxolopyridyl group, a furopyridinyl group, a dihydrodioxynopyridyl group, or a dihydropyridooxazinyl group.

The bicyclic nitrogen- and sulfur-containing heterocyclic ring group refers to a bicyclic nitrogen- and sulfur-containing heterocyclic ring group which contains a nitrogen atom and a sulfur atom as heteroatoms forming the ring, such as a benzothiazolyl group, a benzoisothiazolyl group, or a benzothiadiazolyl group.

The bicyclic heterocyclic ring group refers to a bicyclic nitrogen-containing heterocyclic ring group, a bicyclic oxygen-containing heterocyclic ring group, a bicyclic sulfur-containing heterocyclic ring group, a bicyclic nitrogen- and oxygen-containing heterocyclic ring group, or a bicyclic nitrogen- and sulfur-containing heterocyclic ring group.

The spiro heterocyclic ring group refers to a spiro heterocyclic ring group which contains a nitrogen atom, an oxygen atom, or a sulfur atom as a heteroatom forming the ring, such as a 2-oxa-6-azaspiro[3.3]heptyl group, a 1,4-dioxaspiro[4.5]decyl group, a 1-oxa-8-azaspiro [4.5]decyl group, or a 1-thia-8-azaspiro [4.5]decyl group.

The bridged heterocyclic ring group refers to a bridged heterocyclic ring group which contains a nitrogen atom, an oxygen atom, or a sulfur atom as a heteroatom forming the ring, such as a 3-oxa-8-azabicyclo[3.2.1]octyl group, an 8-oxa-3-azabicyclo[3.2.1]octyl group, or a quinuclidinyl group.

The heterocyclic ring group refers to a monocyclic heterocyclic ring group, a bicyclic heterocyclic ring group, a spiro heterocyclic ring group, or a bridged heterocyclic ring group.

The heterocyclic oxy group refers to a substituent in which an oxygen atom is bonded to a heterocyclic ring group such as pyrrolidinyloxy, piperidinyloxy, tetrahydrofuranyloxy, tetrahydropyranyloxy, or tetrahydrothiopyranyloxy.

The 5- to 10-membered nitrogen- and phosphorus-containing heterocyclic ring refers to a 5- to 10-membered nitrogen- and phosphorus-containing heterocyclic ring which contains only a nitrogen atom and a phosphorus atom as heteroatoms forming the ring and which may be fused, such as 1,3,2-diazaphospholidine, 1,3,2-diazaphosphinane, 1,3,2-diazaphosphepane, or 1,3,2-diazaphosphocane.

The 5- to 10-membered oxygen- and phosphorus-containing heterocyclic ring refers to a 5- to 10-membered oxygen- and phosphorus-containing heterocyclic ring which contains only an oxygen atom and a phosphorus atom as heteroatoms forming the ring and which may be fused, such as 1,3,2-dioxaphospholane, 1,3,2-dioxaphosphinane, 1,3,2-dioxaphosphepane, 1,3,2-dioxaphosphocane, benzo[d][1,3,2]dioxaphosphor, or 4H-benzo[d][1,3,2]dioxaphosphinine.

The 5- to 10-membered nitrogen-, oxygen-, and phosphorus-containing heterocyclic ring refers to a 5- to 10-membered nitrogen-, oxygen-, and phosphorus-containing heterocyclic ring which contains only a nitrogen atom, an oxygen atom, and a phosphorus atom as heteroatoms forming the ring and which may be fused, such as 1,3,2-oxazaphospholidine, 2,3-dihydrobenzo[d][1,3,2]oxazaphosphor, 1,3,2-oxazaphosphinane, or 3,4-dihydro-4H-benzo[e][1,3,2]oxazaphosphinine.

The 6- to 10-membered oxygen- and phosphorus-containing heterocyclic ring refers to a 6- to 10-membered oxygen- and phosphorus-containing heterocyclic ring which contains only an oxygen atom and a phosphorus atom as heteroatoms forming the ring and which may be fused, such as 1,3,2-dioxaphosphinane, 1,3,2-dioxaphosphepane, or 1,3,2-dioxaphosphocane.

The $C_{2-6}$ alkanoyl group refers to a linear or branched $C_{2-6}$ alkanoyl group such as an acetyl group, a propionyl group, a valeryl group, an isovaleryl group, or a pivaloyl group.

The $C_{3-8}$ cycloalkylcarbonyl group refers to a $C_{3-8}$ cycloalkylcarbonyl group such as a cyclopropylcarbonyl group, a cyclobutylcarbonyl group, a cyclopentylcarbonyl group, a cyclohexylcarbonyl group, or a cycloheptylcarbonyl group.

The aroyl group refers to a benzoyl group, a naphthoyl group, or the like.

The heterocyclic carbonyl group refers to a heterocyclic carbonyl group such as pyrrolylcarbonyl, pyridylcarbonyl, furanylcarbonyl, or thienylcarbonyl.

The acyl group refers to a formyl group, a succinyl group, a glutaryl group, a maleoyl group, a phthaloyl group, a $C_{2-6}$ alkanoyl group, a $C_{3-8}$ cycloalkylcarbonyl group, an aroyl group, or a heterocyclic carbonyl group.

The $C_{2-6}$ alkanoyloxy group refers to a linear or branched $C_{2-6}$ alkanoyloxy group such as an acetyloxy group, a propionyloxy group, a valeryloxy group, an isovaleryloxy group, or a pivaloyloxy group.

The $C_{1-6}$ alkylcarbonyloxy group refers to a linear or branched $C_{1-6}$ alkylcarbonyloxy group such as a methylcarbonyloxy group, an ethylcarbonyloxy group, a propylcarbonyloxy group, an isopropylcarbonyloxy group, a butylcarbonyloxy group, a sec-butylcarbonyloxy group, an isobutylcarbonyloxy group, or a tert-butylcarbonyloxy group.

The $C_{3-8}$ cycloalkylcarbonyloxy group refers to a $C_{3-8}$ cycloalkylcarbonyloxy group such as a cyclopropylcarbonyloxy group, a cyclobutylcarbonyloxy group, a cyclopentylcarbonyloxy group, a cyclohexylcarbonyloxy group, or a cycloheptylcarbonyloxy group.

The aroyloxy group refers to a benzoyloxy group, a naphthoyloxy group, or the like.

The heterocyclic carbonyloxy group refers to a heterocyclic carbonyloxy group such as pyrrolylcarbonyloxy, pyridylcarbonyloxy, furanylcarbonyloxy, or thienylcarbonyloxy.

The acyloxy group refers to a $C_{2-6}$ alkanoyloxy group, a $C_{3-8}$ cycloalkylcarbonyloxy group, an aroyloxy group, or a heterocyclic carbonyloxy group.

The $C_{2-6}$ alkanoylthio group refers to a linear or branched $C_{2-6}$ alkanoylthio group such as an acetylthio group, a propionylthio group, a valerylthio group, an isovalerylthio group, or a pivaloylthio group.

The $C_{1-6}$ alkylcarbonylthio group refers to a linear or branched $C_{1-6}$ alkylcarbonylthio group such as a methylcarbonylthio group, an ethylcarbonylthio group, a propylcarbonylthio group, an isopropylcarbonylthio group, a butylcarbonylthio group, a sec-butylcarbonylthio group, an isobutylcarbonylthio group, or a tert-butylcarbonylthio group.

The C$_{3-8}$ cycloalkylcarbonylthio group refers to a C$_{3-8}$ cycloalkylcarbonylthio group such as a cyclopropylcarbonylthio group, a cyclobutylcarbonylthio group, a cyclopentylcarbonylthio group, a cyclohexylcarbonylthio group, or a cycloheptylcarbonylthio group.

The aroylthio group refers to a benzoylthio group, a naphthoylthio group, or the like.

The heterocyclic carbonylthio group refers to a heterocyclic carbonylthio group such as pyrrolylcarbonylthio, pyridylcarbonylthio, furanylcarbonylthio, or thienylcarbonylthio.

The acylthio group refers to a C$_{2-6}$ alkanoylthio group, a C$_{3-8}$ cycloalkylcarbonylthio group, an aroylthio group, or a heterocyclic carbonylthio group.

The silyl group refers to trimethylsilyl, triethylsilyl, a tributylsilyl group, or tert-butylmethylsilyl.

The leaving group refers to a halogen atom, a C$_{1-6}$ alkylsulfonyloxy group, an aryloxy group, or an arylsulfonyloxy group. The C$_{1-6}$ alkylsulfonyloxy group, aryloxy group, and arylsulfonyloxy group may be substituted with one or more substituents selected from a halogen atom, a nitro group, a C$_{1-6}$ alkyl group, and a C$_{1-6}$ alkoxy group.

The hydroxyl protecting group is any conventional group which can be used as a protecting group for a hydroxyl group, and examples thereof include the groups described in, for example, T. W. Greene et al., Protective Groups in Organic Synthesis, 4th edition, pp. 16 to 299, 2007, John Wiley & Sons, Inc. Specific examples of the hydroxyl protecting group include a C$_{1-6}$ alkyl group, a C$_{2-6}$ alkenyl group, an ar-C$_{1-6}$ alkyl group, a C$_{1-6}$ alkoxy C$_{1-6}$ alkyl group, an ar-C$_{1-6}$ alkoxy C$_{1-6}$ alkyl group, an acyl group, a C$_{1-6}$ alkoxycarbonyl group, an ar-C$_{1-6}$ alkoxycarbonyl group, a C$_{1-6}$ alkylsulfonyl group, an arylsulfonyl group, a silyl group, a tetrahydrofuranyl group, and a tetrahydropyranyl group.

The thiol protecting group is any conventional group which can be used as a protecting group for a thiol group, and examples thereof include the groups described in, for example, W. Greene et al., Protective Groups in Organic Synthesis, 4th edition, pp. 647 to 695, 2007, John Wiley & Sons, Inc. Specific examples of the thiol protecting group include a C$_{1-6}$ alkyl group, a C$_{2-6}$ alkenyl group, an ar-C$_{1-6}$ alkyl group, a C$_{1-6}$ alkoxy C$_{1-6}$ alkyl group, an acyl group, and a silyl group.

The amino protecting group is any conventional group which can be used as a protecting group for an amino group, and examples thereof include the groups described in, for example, W. Greene et al., Protective Groups in Organic Synthesis, 4th edition, pp. 696 to 926, 2007, John Wiley & Sons, Inc. Specific examples of the amino protecting group include an ar-C$_{1-6}$ alkyl group, a C$_{1-6}$ alkoxy C$_{1-6}$ alkyl group, an acyl group, a C$_{1-6}$ alkoxycarbonyl group, an ar-C$_{1-6}$ alkoxycarbonyl group, an aryloxycarbonyl group, a C$_{1-6}$ alkylsulfonyl group, an arylsulfonyl group, and a silyl group.

Aliphatic hydrocarbons refer to pentane, hexane, heptane, cyclohexane, methylcyclohexane, and ethylcyclohexane.

Halogenated hydrocarbons refer to dichloromethane, chloroform, and dichloroethane.

Ethers refer to diethyl ether, diisopropyl ether, dioxane, tetrahydrofuran, anisole, ethylene glycol dimethyl ether, diethylene glycol dimethyl ether, and diethylene glycol diethyl ether.

Ketones refer to acetone, 2-butanone, 4-methyl-2-pentanone, and methyl isobutyl ketone.

Esters refer to methyl acetate, ethyl acetate, propyl acetate, and butyl acetate.

Amides refer to N,N-dimethylformamide, N,N-dimethylacetamide, and N-methylpyrrolidone.

Nitriles refer to acetonitrile and propionitrile.

Sulfoxides refer to dimethyl sulfoxide and sulfolane.

Aromatic hydrocarbons refer to benzene, toluene, and xylene.

The inorganic base refers to sodium hydroxide, potassium hydroxide, sodium methoxide, sodium ethoxide, tert-butoxy sodium, tert-butoxy potassium, sodium hydrogen carbonate, sodium carbonate, potassium carbonate, tripotassium phosphate, potassium acetate, cesium fluoride, cesium carbonate, or tert-butyl magnesium chloride.

The organic base refers to triethylamine, N,N-diisopropylethylamine, 1,8-diazabicyclo (5.4.0)undec-7-ene (DBU), pyridine, 4-dimethylaminopyridine, N-methylmorpholine, or imidazole.

Individual substituent groups have the following meanings.

<Substituent group A> a halogen atom; a hydroxyl group which may be protected; a cyano group; a nitro group; a carbamoyl group; an oxo group; a C$_{1-6}$ alkyl group which may be substituted with one or more substituents selected from Substituent group B; a C$_{1-6}$ alkyldisulfanyl group which may be substituted with one or more substituents selected from Substituent group B; a C$_{2-6}$ alkenyl group which may be substituted with one or more substituents selected from Substituent group B; a C$_{2-6}$ alkynyl group which may be substituted with one or more substituents selected from Substituent group B; a C$_{3-8}$ cycloalkyl group which may be substituted with one or more substituents selected from Substituent group B; a C$_{3-8}$ cycloalkyldisulfanyl group which may be substituted with one or more substituents selected from Substituent group B; a C$_{1-6}$ alkoxy group which may be substituted with one or more substituents selected from Substituent group B; a C$_{1-6}$ alkoxycarbonyloxy group which may be substituted with one or more substituents selected from Substituent group B; a C$_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

<Substituent group B> a halogen atom; a hydroxyl group; a cyano group; a nitro group; a carboxyl group; a carbamoyl group; a hydroxymethyl group; a C$_{1-6}$ alkyl group; a C$_{2-6}$ alkenyl group; a C$_{2-6}$ alkynyl group; a C$_{3-8}$ cycloalkyl group; a C$_{1-6}$ alkoxy group; a C$_{1-6}$ alkoxycarbonyl group; a C$_{3-8}$ cycloalkoxycarbonyl group; an ar-C$_{1-6}$ alkoxycarbonyl group; an aryl group; an aryloxy group; a heterocyclic oxy group which may be substituted with one or more substituents selected from a hydroxyl group and a hydroxymethyl group; an ar-$C_{1-6}$ alkoxy group; and an acyloxy group.

Examples of salts of the compound represented by General Formula [1] include salts in basic groups such as an amino group, and salts in acidic groups such as a hydroxyl group and a carboxyl group, which are commonly known.

Examples of salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of salts in acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the salts mentioned above, preferred salts include pharmacologically acceptable salts.

The compound represented by General Formula [1] or a salt thereof according to the embodiment of the present invention can be used for the treatment of adenovirus.

The treatment refers to preventing, treating, or the like of a variety of diseases.

The treatment agent refers to a substance which is provided for the purpose of preventing or treating a variety of diseases.

The preventing refers to inhibition of disease onset, reduction of disease onset risk, delay of disease onset, or the like.

The treating refers to improvement of, inhibition of progression of, or the like of a target disease or condition.

The compound represented by General Formula [1] according to the embodiment of the present invention is represented by

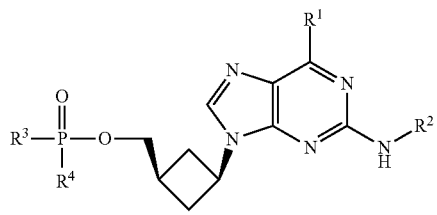

[1]

(in the formula, $R^1$, $R^2$, $R^3$, and $R^4$ are as defined above).

$R^1$ $R^1$ is a halogen atom, an amino group which may be substituted, a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected.

$R^1$ is preferably a halogen atom, an amino group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylthio group which may be substituted with one or more substituents selected from Substituent group A, a hydroxyl group which may be protected, or a thiol group which may be protected; more preferably a halogen atom, an amino group which may be substituted with one or more substituents selected from Substituent group A, a $C_{1-6}$ alkoxy group which may be substituted with one or more substituents selected from Substituent group A, a hydroxyl group which may be protected, or a thiol group which may be protected; still more preferably a halogen atom, an amino group which may be substituted with one or more substituents selected from Substituent group A, a $C_{1-6}$ alkoxy group which may be substituted with one or more substituents selected from Substituent group A, or a hydroxyl group; and even still more preferably a halogen atom or a $C_{1-6}$ alkoxy group.

The substituent of the amino group which may be substituted with one or more substituents selected from Substituent group A in the definition of $R^1$ is preferably a $C_{1-6}$ alkyl group which may be substituted with one or more substituents selected from Substituent group B or a $C_{3-8}$ cycloalkyl group which may be substituted with one or more substituents selected from Substituent group B, and more preferably a $C_{1-6}$ alkyl group or a $C_{3-8}$ cycloalkyl group.

The substituent of the $C_{1-6}$ alkoxy group which may be substituted with one or more substituents selected from Substituent group A in the definition of $R^1$ is preferably a halogen atom.

The substituent of the $C_{3-8}$ cycloalkoxy group which may be substituted with one or more substituents selected from Substituent group A in the definition of $R^1$ is preferably a halogen atom or a $C_{1-6}$ alkyl group which may be substituted with one or more substituents selected from Substituent group B.

The substituent of the $C_{1-6}$ alkylthio group which may be substituted with one or more substituents selected from Substituent group A in the definition of $R^1$ is preferably a halogen atom or a $C_{1-6}$ alkoxy group which may be substituted with one or more substituents selected from Substituent group B.

$R^2$ $R^2$ is a hydrogen atom or an amino protecting group.

$R^2$ is preferably a hydrogen atom or an acyl group, more preferably a hydrogen atom or a $C_{2-6}$ alkanoyl group, and still more preferably a hydrogen atom.

$R^3$ $R^3$ is a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or —O—P(O)(OH)—O—$PO_3H$, provided that $R^2$ is a hydrogen atom in a case where $R^3$ is —O—P(O)(OH)—O—$PO_3H$.

$R^3$ is preferably a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or —O—P(O)(OH)—O—PO$_3$H; more preferably a C$_{1-20}$ alkoxy group which may be substituted with one or more substituents selected from Substituent group A, a C$_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or —O—P(O)(OH)—O—PO$_3$H; still more preferably a C$_{1-20}$ alkoxy group which may be substituted with one or more substituents selected from Substituent group A, a C$_{1-20}$ alkylthio group which may be substituted with one or more substituents selected from Substituent group A, an aryloxy group which may be substituted with one or more substituents selected from Substituent group A, or —O—P(O)(OH)—O—PO$_3$H; and even still more preferably a C$_{1-20}$ alkoxy group which may be substituted with one or more substituents selected from Substituent group A, an aryloxy group which may be substituted with one or more substituents selected from Substituent group A, or —O—P(O)(OH)—O—PO$_3$H.

The substituent of the C$_{1-20}$ alkoxy group which may be substituted with one or more substituents selected from Substituent group A in the definition of R$^3$ is preferably a C$_{1-6}$ alkyldisulfanyl group which may be substituted with one or more substituents selected from Substituent group B, a C$_{1-6}$ alkylcarbonyloxy group which may be substituted with one or more substituents selected from Substituent group B, or a C$_{1-6}$ alkylcarbonylthio group which may be substituted with one or more substituents selected from Substituent group B.

Here, the substituent of the C$_{1-6}$ alkyldisulfanyl group which may be substituted with one or more substituents selected from Substituent group B is preferably a hydroxyl group, a C$_{1-6}$ alkoxy group, an ar-C$_{1-6}$ alkoxy group, or an acyloxy group and more preferably an ar-C$_{1-6}$ alkoxy group.

The substituent of the C$_{1-6}$ alkylcarbonyloxy group which may be substituted with one or more substituents selected from Substituent group B is preferably a hydroxyl group, a C$_{1-6}$ alkoxy group, an ar-C$_{1-6}$ alkoxy group, or an acyloxy group and more preferably a hydroxyl group.

The substituent of the C$_{1-6}$ alkylcarbonylthio group which may be substituted with one or more substituents selected from Substituent group B is preferably a hydroxyl group, a C$_{1-6}$ alkoxy group, an ar-C$_{1-6}$ alkoxy group, or an acyloxy group and more preferably a hydroxyl group.

The substituent of the aryloxy group which may be substituted with one or more substituents selected from Substituent group A in the definition of R$^3$ is preferably a halogen atom, a C$_{1-6}$ alkyl group which may be substituted with one or more substituents selected from Substituent group B, or a C$_{1-6}$ alkoxy group which may be substituted with one or more substituents selected from Substituent group B, and more preferably a halogen atom.

R$^4$

R$^4$ is a C$_{1-20}$ alkoxy group which may be substituted, a C$_{3-8}$ cycloalkoxy group which may be substituted, a C$_{1-20}$ alkylthio group which may be substituted, an aryloxy group which may be substituted, a heterocyclic ring group which may be substituted, a heterocyclic oxy group which may be substituted, an amino group which may be substituted, or a hydroxyl group which may be protected.

R$^4$ is preferably a C$_{1-20}$ alkoxy group which may be substituted with one or more substituents selected from Substituent group A, a C$_{3-8}$ cycloalkoxy group which may be substituted with one or more substituents selected from Substituent group A, a C$_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or a hydroxyl group which may be protected; more preferably a C$_{1-20}$ alkoxy group which may be substituted with one or more substituents selected from Substituent group A, a C$_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected; and still more preferably a C$_{1-20}$ alkoxy group which may be substituted with one or more substituents selected from Substituent group A, an amino group which may be substituted with one or more substituents selected from Substituent group A, or a hydroxyl group which may be protected.

The substituent of the C$_{1-20}$ alkoxy group which may be substituted with one or more substituents selected from Substituent group A in the definition of R$^4$ is preferably a C$_{1-6}$ alkyldisulfanyl group which may be substituted with one or more substituents selected from Substituent group B, a C$_{1-6}$ alkylcarbonyloxy group which may be substituted with one or more substituents selected from Substituent group B, or a C$_{1-6}$ alkylcarbonylthio group which may be substituted with one or more substituents selected from Substituent group B.

Here, the substituent of the C$_{1-6}$ alkyldisulfanyl group which may be substituted with one or more substituents selected from Substituent group B is preferably a hydroxyl group, a C$_{1-6}$ alkoxy group, an ar-C$_{1-6}$ alkoxy group, or an acyloxy group and more preferably an ar-C$_{1-6}$ alkoxy group.

The substituent of the C$_{1-6}$ alkylcarbonyloxy group which may be substituted with one or more substituents selected from Substituent group B is preferably a hydroxyl group, a C$_{1-6}$ alkoxy group, an ar-C$_{1-6}$ alkoxy group, or an acyloxy group and more preferably a hydroxyl group.

The substituent of the C$_{1-6}$ alkylcarbonylthio group which may be substituted with one or more substituents selected from Substituent group B is preferably a hydroxyl group, a C$_{1-6}$ alkoxy group, an ar-C$_{1-6}$ alkoxy group, or an acyloxy group and more preferably a hydroxyl group.

The substituent of the aryloxy group which may be substituted with one or more substituents selected from Substituent group A in the definition of R$^4$ is preferably a halogen atom, a C$_{1-6}$ alkyl group which may be substituted with one or more substituents selected from Substituent group B, or a C$_{1-6}$ alkoxy group which may be substituted with one or more substituents selected from Substituent group B, and more preferably a halogen atom.

R$^3$ and R$^4$, together with the phosphorus atom to which R$^3$ and R$^4$ are bonded, may be combined to form a 5- to 10-membered nitrogen- and phosphorus-containing heterocyclic ring which may be substituted, a 5- to 10-membered oxygen- and phosphorus-containing heterocyclic ring which may be substituted, or a 5- to 10-membered nitrogen-, oxygen-, and phosphorus-containing heterocyclic ring which may be substituted.

The ring formed by combining $R^3$ and $R^4$ together with the phosphorus atom to which $R^3$ and $R^4$ are bonded is preferably a 5- to 10-membered oxygen- and phosphorus-containing heterocyclic ring which may be substituted and more preferably 1,3,2-dioxaphosphinane or 4H-benzo[d][1,3,2]dioxaphosphinine.

The substituent of the 5- to 10-membered nitrogen- and phosphorus-containing heterocyclic ring which may be substituted, the 5- to 10-membered oxygen- and phosphorus-containing heterocyclic ring which may be substituted, or the 5- to 10-membered nitrogen-, oxygen-, and phosphorus-containing heterocyclic ring which may be substituted, each of which being formed by combining $R^3$ and $R^4$ together with the phosphorus atom to which $R^3$ and $R^4$ are bonded, is preferably a $C_{1-6}$ alkoxy group which may be substituted with one or more substituents selected from Substituent group A or an aryl group which may be substituted with one or more substituents selected from Substituent group A.

Here, the substituent of the aryl group which may be substituted with one or more substituents selected from Substituent group A is preferably a halogen atom.

The compound represented by General Formula [1] is preferably a compound in which $R^1$ is a halogen atom, an amino group which may be substituted with one or more substituents selected from Substituent group A, a $C_{1-6}$ alkoxy group which may be substituted with one or more substituents selected from Substituent group A, a hydroxyl group which may be protected, or a thiol group which may be protected; $R^2$ is a hydrogen atom; $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or —O—P(O)(OH)—O—PO$_3$H; and $R^4$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected.

The compound represented by General Formula [1] is more preferably a compound in which $R^1$ is a halogen atom, an amino group which may be substituted with one or more substituents selected from Substituent group A, a $C_{1-6}$ alkoxy group which may be substituted with one or more substituents selected from Substituent group A, or a hydroxyl group; $R^2$ is a hydrogen atom; $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, or —O—P(O)(OH)—O—PO$_3$H; and $R^4$ is a $C_{1-20}$ alkoxy group which may be substituted with one or more substituents selected from Substituent group A, an amino group which may be substituted with one or more substituents selected from Substituent group A, or a hydroxyl group which may be protected.

The compound represented by General Formula [1] is still more preferably a compound in which $R^1$ is a halogen atom or a $C_{1-6}$ alkoxy group; $R^2$ is a hydrogen atom; $R^3$ is a $C_{1-20}$ alkoxy group which may be substituted with one or more substituents selected from Substituent group A, an aryloxy group which may be substituted with one or more substituents selected from Substituent group A, or —O—P(O)(OH)—O—PO$_3$H; and $R^4$ is a $C_{1-20}$ alkoxy group which may be substituted with one or more substituents selected from Substituent group A, an amino group which may be substituted with one or more substituents selected from Substituent group A, or a hydroxyl group which may be protected.

The compound represented by General Formula [1] is preferably methyl (((cis-3-(2-amino-6-methoxy-9H-purin-9-yl)cyclobutyl)methoxy)(phenoxy)phosphoryl)-L-alaninate (Example 3-2-2), methyl (((cis-3-(2-amino-6-methoxy-9H-purin-9-yl)cyclobutyl)methoxy)(naphthalen-1-yloxy) phosphoryl)-L-alaninate (Example 1-2-1), methyl (((cis-3-(2-amino-6-methoxy-9H-purin-9-yl)cyclobutyl)methoxy) (4-chlorophenoxy)phosphoryl)-L-alaninate (Example 1-2-2), methyl (((cis-3-(2-amino-6-methoxy-9H-purin-9-yl) cyclobutyl)methoxy)(4-bromophenoxy)phosphoryl)-L-alaninate (Example 1-1), ethyl (((cis-3-(2-amino-6-methoxy-9H-purin-9-yl)cyclobutyl)methoxy)(4-bromophenoxy)phosphoryl)-L-alaninate (Example 1-2-7), ethyl (((cis-3-(2-amino-6-methoxy-9H-purin-9-yl)cyclobutyl)methoxy)(4-chlorophenoxy)phosphoryl)-L-alaninate (Example 1-2-8), methyl (((cis-3-(2-amino-6-methoxy-9H-purin-9-yl)cyclobutyl)methoxy)(2-bromophenoxy) phosphoryl)-L-alaninate (Example 1-2-9), methyl (((cis-3-(2-amino-6-methoxy-9H-purin-9-yl)cyclobutyl)methoxy) (2-chlorophenoxy)phosphoryl)-L-alaninate (Example 1-2-10), methyl (((cis-3-(2-amino-6-methoxy-9H-purin-9-yl) cyclobutyl)methoxy)(2-(pivaloylthio)ethoxy)phosphoryl)-L-alaninate (Example 1-2-11), methyl (((cis-3-(2-amino-6-ethoxy-9H-purin-9-yl)cyclobutyl)methoxy)(4-bromophenoxy)phosphoryl)-L-alaninate (Example 1-2-19), methyl 2-((((cis-3-(2-amino-6-methoxy-9H-purin-9-yl)cyclobutyl)methoxy)(4-bromophenoxy)phosphoryl)amino)-2-methylpropanoate (Example 1-2-25), (cis-3-(2-amino-6-methoxy-9H-purin-9-yl)cyclobutyl)methyl bis (pivaloyloxymethyl)phosphate (Example 5-2), methyl (((cis-3-(2-amino-6-methoxy-9H-purin-9-yl)cyclobutyl) methoxy)(4-chloro-2-fluorophenoxy) phosphoryl)-L-alaninate (Example 1-2-31), or methyl (((cis-3-(2-amino-6-methoxy-9H-purin-9-yl)cyclobutyl)methoxy)(3-bromophenoxy)phosphoryl)-L-alaninate (Example 1-2-32).

In a case where isomers (for example, a tautomer, an optical isomer, and a geometric isomer) are present for the compound represented by General Formula [1] or a salt thereof, the present invention also includes those isomers and further includes solvates, hydrates, and various forms of crystals.

Next, a method for producing the compound represented by General Formula [1] will be described.

The compound represented by General Formula [1] is produced by combining methods known per se, and can be produced, for example, according to the following production methods.

Production Method 1

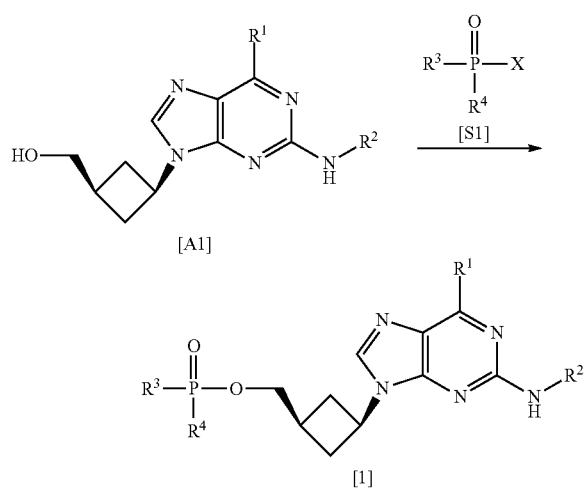

(In the formulae, X represents a leaving group, and $R^1$, $R^2$, $R^3$, and $R^4$ are as defined above.)

As a compound of General Formula [A1], for example, 2-amino-9-(cis-3-(hydroxymethyl)cyclobutyl)-1,9-dihydro-6H-purin-6-one is known.

As a compound of General Formula [S1], for example, ((chlorophosphoryl)bis(oxy))bis(methylene)bis(2,2-dimethylpropanoate) and 2-chloro-4H-benzo[d][1,3,2]dioxaphosphinine 2-oxide are known.

The compound of General Formula [1] can be produced by reacting the compound of General Formula [A1] with the compound of General Formula [S1] in the presence of a base.

The solvent used in this reaction is not particularly limited as long as it does not affect the reaction and examples thereof include ethers and amides. These solvents may be used as a mixture thereof.

Preferred examples of the solvent include ethers, with tetrahydrofuran being more preferred.

The amount of the solvent to be used is not particularly limited, but may be 1 to 50-fold amount (v/w) with respect to the compound of General Formula [A1].

The amount of the compound of General Formula [A1] to be used may be 1 to 20-fold molar amount and preferably 1 to 10-fold molar amount with respect to the compound of General Formula [A1].

The base used in this reaction may be, for example, tert-butyl magnesium chloride.

The amount of the base to be used may be 1 to 5-fold molar amount and preferably 1 to 2-fold molar amount with respect to the compound of General Formula [A1].

This reaction may be carried out at −78° C. to 100° C., preferably −78° C. to 40° C. for 30 minutes to 48 hours.

The compound of General Formula [A1] and the compound of General Formula [S1] can be derived into other compounds of General Formula [A1] and other compounds of General Formula [S1], for example, by subjecting them to a reaction known per se such as condensation, addition, oxidation, reduction, rearrangement, substitution, halogenation, dehydration, or hydrolysis, or an appropriate combination of these reactions.

In a case where an amino group, a hydroxyl group, or a carboxyl group is present in the compounds of General Formula [A1] and intermediates thereof, the protecting group for such a group can be appropriately rearranged to carry out the reaction. In addition, in a case where two or more protecting groups are present, a reaction known per se can be carried out to make selective deprotection.

Among the compounds used in the above-mentioned production method, a compound that can take the form of a salt can also be used as a salt. Examples of such a salt include the same salts as the salts of the compound represented by General Formula [1] according to the embodiment of the present invention described above.

In a case where isomers (for example, a tautomer, an optical isomer, and a geometric isomer) are present for the compounds used in the above-mentioned production method, these isomers can also be used. In addition, in a case where solvates, hydrates, and various forms of crystals are present, these solvates, hydrates, and various forms of crystals can also be used.

The compound represented by General Formula [1] or a salt thereof can be used as an anti-adenoviral agent or as a medicine for treating an adenovirus infection. Examples of the adenovirus infection include respiratory infection, pharyngoconjunctival fever, epidemic keratoconjunctivitis, hepatitis, gastroenteritis, cystitis, and encephalitis. The anti-adenoviral agent according to the embodiment of the present invention and the medicine for treating an adenovirus infection according to the embodiment of the present invention can be provided as a pharmaceutical composition.

In a pharmaceutical composition containing the compound represented by General Formula [1] or a salt thereof according to the embodiment of the present invention, an additive commonly used in formulation may be appropriately mixed.

Examples of the additive include an excipient, a disintegrating agent, a binding agent, a lubricant, a taste masking agent, a colorant, a flavoring agent, a surfactant, a coating agent, and a plasticizer.

Examples of the excipient include sugar alcohols such as erythritol, mannitol, xylitol, and sorbitol; sugars such as white sugar, powdered sugar, lactose, and glucose; cyclodextrins such as α-cyclodextrin, β-cyclodextrin, γ-cyclodextrin, hydroxypropyl β-cyclodextrin, and sodium sulfobutylether β-cyclodextrin; celluloses such as crystalline cellulose and microcrystalline cellulose; and starches such as corn starch, potato starch, and pregelatinized starch.

Examples of the disintegrating agent include carmellose, carmellose calcium, croscarmellose sodium, sodium carboxymethyl starch, crospovidone, low-substituted hydroxypropyl cellulose, and a partially pregelatinized starch.

Examples of the binding agent include hydroxypropyl cellulose, carmellose sodium, and methylcellulose.

Examples of the lubricant include stearic acid, magnesium stearate, calcium stearate, talc, hydrated silicon dioxide, light anhydrous silicic acid, and sucrose fatty acid ester.

Examples of the taste masking agent include aspartame, saccharin, stevia, thaumatin, and acesulfame potassium.

Examples of the colorant include titanium dioxide, iron sesquioxide, yellow ferric oxide, black iron oxide, Food Red No. 102, Food Yellow No. 4, and Food Yellow No. 5.

Examples of the flavoring agent include an essential oil such as an orange oil, a lemon oil, a peppermint oil, or a pine oil; an essence such as an orange essence or a peppermint essence; a flavor such as a cherry flavor, a vanilla flavor, or a fruit flavor; a powder fragrance such as an apple micron, a banana micron, a peach micron, a strawberry micron, or an orange micron; vanillin; and ethyl vanillin.

Examples of the surfactant include sodium lauryl sulfate, dioctyl sodium sulfosuccinate, polysorbate, and polyoxyethylene hydrogenated castor oil.

Examples of the coating agent include hydroxypropyl methyl cellulose, an aminoalkyl methacrylate copolymer E, an aminoalkyl methacrylate copolymer RS, ethyl cellulose, cellulose acetate phthalate, hydroxypropyl methyl cellulose phthalate, a methacrylic acid copolymer L, a methacrylic acid copolymer LD, and a methacrylic acid copolymer S.

Examples of the plasticizer include triethyl citrate, macrogol, triacetin, and propylene glycol.

These additives may be used alone or in combination of two or more thereof.

Although the formulation amount of the additives is not particularly limited, the additives may be suitably formulated such that the effects thereof are sufficiently exhibited depending on the respective purposes.

The pharmaceutical composition to which an appropriate mixture has been added can be orally or parenterally administered according to a conventional method in the form of a tablet, a capsule, a powder, a syrup, a granule, a pill, a suspension, an emulsion, a solution, a powdered preparation, a suppository, an eye drop, a nasal drop, an ear drop, a patch, an ointment, an injection, or the like, and is preferably parenterally administered in the form of eye drop or the like.

The administration method, dosage, and administration frequency of the compound represented by General Formula [1] or the salt thereof according to the embodiment of the present invention can be appropriately selected depending on the age, body weight, and symptoms of the patient. Typically, for an adult, 0.01 to 1,000 mg/kg/day may be administered orally or parenterally once or in several divided doses. It is preferred that 0.01 to 1,000 mg/kg/day is administered parenterally in the form of eye drop or the like once or in several divided doses.

Examples

Hereinafter, the present invention will be described with reference to Reference Examples and Examples, but the present invention is not limited thereto.

Unless otherwise specified, purification by column chromatography was carried out using an automated purification apparatus ISOLERA (manufactured by Biotage AB) or a medium-pressure liquid chromatograph YFLC-Wprep2XY.N (manufactured by Yamazen Corporation).

Unless otherwise specified, SNAPKP-Sil Cartridge (manufactured by Biotage AB), or HI-FLASH COLUMN W001, W002, W003, W004, or W005 (manufactured by Yamazen Corporation) was used as a carrier in silica gel column chromatography; SNAP KP-NH Cartridge (manufactured by Biotage AB) was used as a carrier in basic silica gel column chromatography; and CHROMATOREX Q-PACK Cartridge (manufactured by Fuji Silysia Chemical Ltd.) was used as a carrier in diol silica gel column chromatography.

In preparative thin layer chromatography, PLC glass plate silica gel $F_{60}$ (manufactured by Merck & Co., Inc.) was used.

The mixing ratio in the eluent was a volume ratio. For example, "hexane:ethyl acetate gradient elution=50:50 to 0:100" means that an eluent of 50% hexane/50% ethyl acetate was finally changed to an eluent of 0% hexane/100% ethyl acetate.

In addition, for example, "hexane:ethyl acetate gradient elution=50:50 to 0:100, methanol:ethyl acetate gradient elution=0:100 to 20:80" means that an eluent of 50% hexane/50% ethyl acetate was changed to an eluent of 0% hexane/100% ethyl acetate, and then the eluent was switched to an eluent of 0% methanol/100% ethyl acetate and finally changed to an eluent of 20% methanol/80% ethyl acetate.

SFC 30 (manufactured by Waters Corporation) was used for supercritical fluid chromatography.

MS spectra were measured using an ACQUITY SQD LC/MS System (manufactured by Waters Corporation, ionization method: Electro Spray Ionization (ESI) method), a Model M-8000 (manufactured by Hitachi, Ltd., ionization method: ESI method), or an LCMS-2010EV (manufactured by Shimadzu Corporation, ionization method: method of carrying out ESI and Atmospheric Pressure Chemical Ionization (APCI) at the same time).

As a microwave reactor, Initiator Sixty (manufactured by Biotage AB) was used.

NMR spectra were measured using Bruker AV300 (manufactured by Bruker Corporation, 300 MHz) and using tetramethylsilane as an internal standard, and all δ values were shown in ppm.

The retention time (RT) was measured using SQD (manufactured by Waters Corporation), and was shown in minutes (min).

Column: BEHC 18 1.7 μm, 2.1×30 mm (manufactured by Waters Corporation)
Solvent: liquid A: 0.1% formic acid-water
liquid B: 0.1% formic acid-acetonitrile
Gradient cycle: 0.00 min (liquid A/liquid B=95/5), 2.00 min (liquid A/liquid B=5/95), 3.00 min (liquid A/liquid B=5/95), 3.01 min (liquid A/liquid B=100/0), 3.80 min (liquid A/liquid B=100/0)
Flow rate: 0.5 mL/min
Column temperature: room temperature
Detection wavelength: 254 nm
Abbreviations in Examples have the following meanings.
Boc: tert-butoxycarbonyl
Et: ethyl
HATU: 1-(bis(dimethylamino)methylene)-1H-1,2,3-triazolo[4,5, b]pyridinium 3-oxide hexafluorophosphate
M: mol/L
Me: methyl
Pr: propyl
RT (min): retention time (min)
*: bonding position Reference Example 1

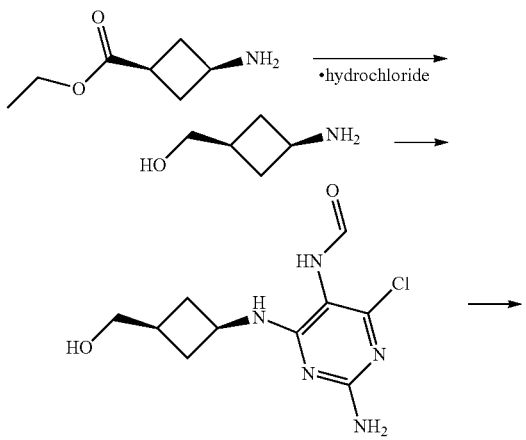

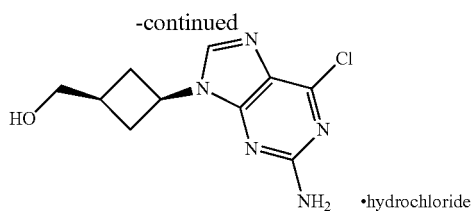

First Step

Under a nitrogen atmosphere, a 2.0 M lithium aluminum hydride/tetrahydrofuran solution (25 mL) was added dropwise under ice-cooling to a mixture of ethyl cis-3-aminocyclobutane-1-carboxylate hydrochloride (4.3 g) and tetrahydrofuran (43 mL) which was then stirred at room temperature for 1 hour. Water (4 mL), a 15% aqueous sodium hydroxide solution (4 mL), and water (12 mL) were added to the reaction solution, and the resulting solid was filtered off and washed with tetrahydrofuran. The solvent was distilled off under reduced pressure to give (cis-3-aminocyclobutyl)methanol (4.4 g) as a colorless oil.

Second Step

A mixture of (cis-3-aminocyclobutyl)methanol (8.5 g) obtained in the first step, 2-amino-4,6-dichloro-5-formamidopyrimidine (17.4 g), N,N-diisopropylethylamine (73 mL), ethanol (255 mL), and N-methyl-2-pyrrolidone (8.5 mL) was stirred with heating under reflux for 6 hours. The solvent was distilled off under reduced pressure, and the obtained residue was purified by silica gel column chromatography (methanol:ethyl acetate=5:95) to give N-(2-amino-4-chloro-6-(((cis-3-(hydroxymethyl)cyclobutyl)amino)pyrimidine-5-formamide (8.0 g) as a yellow solid.

MS (ESI m/z): 272, 274 (M+H)
RT (min): 0.44

Third Step

Triethyl orthoformate (24 mL) and a 4 M hydrochloric acid/dioxane solution (11 mL) were added to a mixture of N-(2-amino-4-chloro-6-(((cis-3-(hydroxymethyl)cyclobutyl)amino)pyrimidine-5-formamide (7.9 g) and ethanol (40 mL) which was then stirred at 53° C. for 2 hours. A 4 M hydrochloric acid/dioxane solution (7.2 mL) was added to the reaction solution which was then stirred at 53° C. for 9 hours. Isopropyl alcohol (60 mL) was added to the reaction solution which was then stirred for 2 hours under ice-cooling, and the resulting solid was collected by filtration. A mixture of the obtained crude product (5.8 g), ethanol (35 mL), and water (1.7 mL) was stirred at 50° C. for 30 minutes. After cooling to room temperature, the solid was collected by filtration and washed with ethanol to give (cis-3-(2-amino-6-chloro-9H-purin-9-yl)cyclobutyl)methanol hydrochloride (3.5 g) as a pale yellow solid.

MS (ESI m/z): 254, 256 (M+H)
RT (min): 0.61

Reference Example 2-1

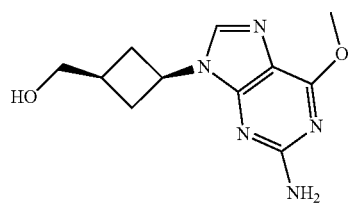 [SMILES: COc1nc(N)nc2c1ncn2[C@H]1C[C@@H](CO)C1]

A 5 M sodium methoxide/methanol solution (0.5 mL) was added to a mixture of (cis-3-(2-amino-6-chloro-9H-purin-9-yl)cyclobutyl)methanol hydrochloride (336 mg) and methanol (4.0 mL) which was then stirred at 50° C. for 5 hours. The solvent was distilled off under reduced pressure, and the obtained residue was purified by silica gel column chromatography (hexane:ethyl acetate=50:50 to 0:100, methanol:ethyl acetate=0:100 to 20:80) to give (cis-3-(2-amino-6-methoxy-9H-purin-9-yl)cyclobutyl)methanol (142 mg) as a white solid.

MS (ESI m/z): 250 (M+H)
RT (min): 0.54

Reference Example 2-2

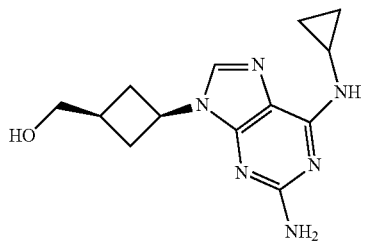 [SMILES: Nc1nc(NC2CC2)c2ncn([C@H]3C[C@@H](CO)C3)c2n1]

Cyclopropylamine (50 μL) was added to a mixture of (cis-3-(2-amino-6-chloro-9H-purin-9-yl)cyclobutyl)methanol hydrochloride (20 mg) and ethanol (0.5 mL) which was then irradiated with microwave (microwave reactor, 120° C., 1 hour, 2.45 GHz, 0 to 240 W). The reaction solution was purified by silica gel column chromatography (hexane:ethyl acetate=50:50 to 0:100, methanol:ethyl acetate=0:100 to 20:80) to give (cis-3-(2-amino-6-(cyclopropylamino)-9H-purin-9-yl)cyclobutyl)methanol (21 mg) as a white solid.

MS (ESI m/z): 275 (M+H)
RT (min): 0.55

Reference Example 2-3

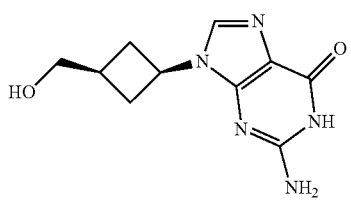 [SMILES: Nc1nc2c(ncn2[C@H]2C[C@@H](CO)C2)c(=O)[nH]1]

A mixture of (cis-3-(2-amino-6-chloro-9H-purin-9-yl)cyclobutyl)methanol (0.50 g), water (4.0 mL), and formic acid (4.0 mL) was stirred at 70° C. for 2.5 hours. The solvent was distilled off under reduced pressure, and a 7 M ammonia/methanol solution (10 mL) was added to the obtained residue which was then allowed to stand for 12 hours. The solvent was distilled off under reduced pressure, methanol (2.0 mL) was added to the obtained residue, and the resulting solid was collected by filtration to give 2-amino-9-(cis-3-(hydroxymethyl)cyclobutyl)-1,9-dihydro-6H-purin-6-one (0.36 g) as a white solid.

MS (ESI m/z): 236 (M+H)
RT (min): 0.38

Reference Example 2-4

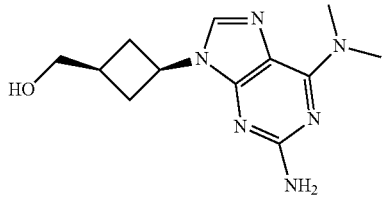 [SMILES: CN(C)c1nc(N)nc2c1ncn2[C@H]1C[C@@H](CO)C1]

A 50% aqueous dimethylamine solution (0.1 mL) was added to a mixture of (cis-3-(2-amino-6-chloro-9H-purin-9-yl)cyclobutyl)methanol hydrochloride (20 mg) and ethanol (0.5 mL) which was then stirred at room temperature for 1 hour. The reaction solution was purified by silica gel column chromatography (hexane:ethyl acetate=50:50 to 0:100, methanol:ethyl acetate=0:100 to 20:80) to give (cis-3-(2-amino-6-(dimethylamino)-9H-purin-9-yl)cyclobutyl)methanol (18 mg) as a white solid.

MS (ESI m/z): 263 (M+H)

RT (min): 0.54

Reference Example 2-5

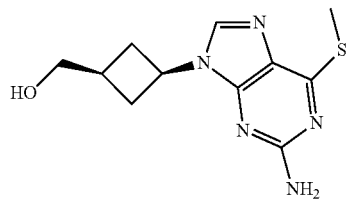

A 15% aqueous sodium thiomethoxide solution (0.1 mL) was added to a mixture of (cis-3-(2-amino-6-chloro-9H-purin-9-yl)cyclobutyl)methanol hydrochloride (20 mg) and ethanol (0.5 mL) which was then stirred at room temperature for 1 hour. The reaction solution was purified by silica gel column chromatography (hexane:ethyl acetate=50:50 to 0:100, methanol:ethyl acetate=0:100 to 20:80) to give (cis-3-(2-amino-6-(methylthio)-9H-purin-9-yl)cyclobutyl) methanol (14 mg) as a white solid.

MS (ESI m/z): 266 (M+H)

RT (min): 0.68

Reference Example 2-6

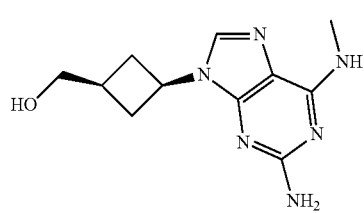 [SMILES: CNc1nc(N)nc2c1ncn2[C@H]1C[C@@H](CO)C1]

A 2 M methylamine/tetrahydrofuran solution (0.2 mL) was added to a mixture of (cis-3-(2-amino-6-chloro-9H-purin-9-yl)cyclobutyl)methanol hydrochloride (20 mg) and ethanol (0.5 mL) which was then irradiated with microwave (microwave reactor, 120° C., 1 hour, 2.45 GHz, 0 to 240 W). The reaction solution was purified by silica gel column chromatography (hexane:ethyl acetate=50:50 to 0:100, methanol:ethyl acetate=0:100 to 20:80) to give (cis-3-(2-amino-6-(methylamino)-9H-purin-9-yl)cyclobutyl)methanol (17 mg) as a white solid.

MS (ESI m/z): 249 (M+H)

RT (min): 0.47

Reference Example 2-7

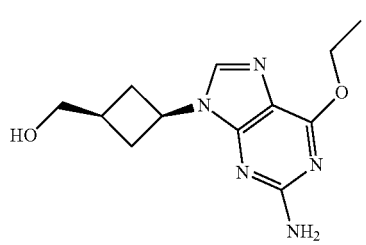 [SMILES: CCOc1nc(N)nc2c1ncn2[C@H]1C[C@@H](CO)C1]

A 20% sodium ethoxide/ethanol solution (0.1 mL) was added to a mixture of (cis-3-(2-amino-6-chloro-9H-purin-9-yl)cyclobutyl)methanol hydrochloride (20 mg) and methanol (0.5 mL) which was then stirred at room temperature for 18 hours. The reaction solution was purified by silica gel column chromatography (hexane:ethyl acetate=50:50 to 0:100, methanol:ethyl acetate=0:100 to 20:80) to give (cis-3-(2-amino-6-ethoxy-9H-purin-9-yl)cyclobutyl)methanol (15 mg) as a white solid.

MS (ESI m/z): 264 (M+H)

RT (min): 0.64

Reference Example 2-8

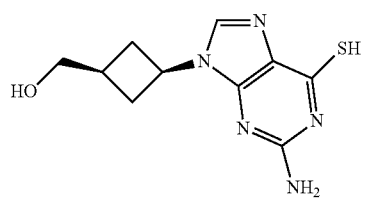 [SMILES: Nc1nc(S)c2ncn([C@H]3C[C@@H](CO)C3)c2n1]

A 15% aqueous sodium hydrosulfide solution (0.1 mL) was added to a mixture of (cis-3-(2-amino-6-chloro-9H-purin-9-yl)cyclobutyl)methanol hydrochloride (20 mg) and ethanol (0.5 mL) which was then stirred at room temperature for 18 hours. The reaction solution was purified by silica gel column chromatography (hexane:ethyl acetate=50:50 to 0:100, methanol:ethyl acetate=0:100 to 20:80) to give (cis-3-(2-amino-6-mercapto-9H-purin-9-yl)cyclobutyl)methanol (15 mg) as a white solid.

MS (ESI m/z): 252 (M+H)

RT (min): 0.47

Reference Example 2-9

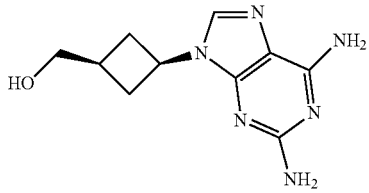 [SMILES: Nc1nc(N)c2ncn([C@H]3C[C@@H](CO)C3)c2n1]

A mixture of (cis-3-(2-amino-6-chloro-9H-purin-9-yl)cyclobutyl)methanol hydrochloride (20 mg) and a 7 M ammonia/methanol solution (0.5 mL) was irradiated with microwave (microwave reactor, 130° C., 3 hours, 2.45 GHz, 0 to 240 W). The reaction solution was purified by basic silica gel column chromatography (hexane:ethyl acetate=50:50 to 0:100, methanol:ethyl acetate=0:100 to 20:80) to give (cis-3-(2,6-diamino-9H-purin-9-yl)cyclobutyl)methanol (15 mg) as a white solid.

MS (ESI m/z): 235 (M+H)
RT (min): 0.40

Reference Example 3-1

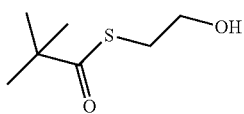

Pivaloyl chloride (1.3 mL) was added dropwise at −78° C. to a mixture of 2-mercaptoethanol (0.75 mL), triethylamine (2.0 mL), and methylene chloride (25 mL) which was then stirred at room temperature for 2 hours. Water (20 mL) was added to the reaction solution, and the organic layer was dried over anhydrous sodium sulfate. The solvent was distilled off under reduced pressure to give S-(2-hydroxyethyl) 2,2-dimethylpropanethioate (1.8 g) as a colorless oil.

1H-NMR (CDCl$_3$) δ: 3.76 (t, 2H, J=6.1 Hz), 3.06 (t, 2H, J=6.1 Hz), 1.93 (br s, 1H), 1.25 (s, 9H).

Reference Example 3-2

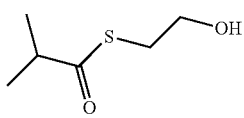

The following compound was obtained in the same manner as in Reference Example 3-1.

S-(2-hydroxyethyl) 2-methylpropanethioate $^1$H-NMR (CDCl$_3$) δ: 3.77 (t, 2H, J=6.3 Hz), 3.08 (t, 2H, J=6.3 Hz), 2.85-2.70 (m, 1H), 1.89 (br s, 1H), 1.21 (d, 6H, J=6.6 Hz).

Reference Example 3-3

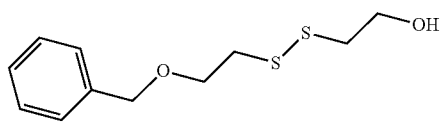 [SMILES: OCCSSCCOCc1ccccc1]

Under a nitrogen atmosphere, 60% sodium hydride (0.13 g) was added to a mixture of 2,2'-disulfanediyldiethanol (0.50 g) and tetrahydrofuran (5.0 mL) which was then stirred at room temperature for 10 minutes. Benzyl bromide (0.38 mL) was added to the reaction solution which was then stirred for 3 hours, and water was added thereto, followed by extraction with ethyl acetate. The organic layer was washed with an aqueous saturated sodium chloride solution, the solvent was distilled off under reduced pressure, and then the obtained residue was purified by silica gel column chromatography (hexane:ethyl acetate=80:20 to 50:50) to give 2-((2-(benzyloxy)ethyl)disulfanyl)ethanol (0.39 g) as a colorless oil.

$^1$H-NMR (CDCl$_3$) δ: 7.39-7.27 (m, 5H), 4.56 (s, 2H), 3.92-3.81 (m, 2H), 3.75 (t, 2H, J=6.3 Hz), 2.94 (t, 2H, J=6.3 Hz), 2.83 (t, 2H, J=5.9 Hz), 2.12-1.95 (m, 1H).

MS (ESI m/z): 245 (M+H)
RT (min): 1.30

Reference Example 4

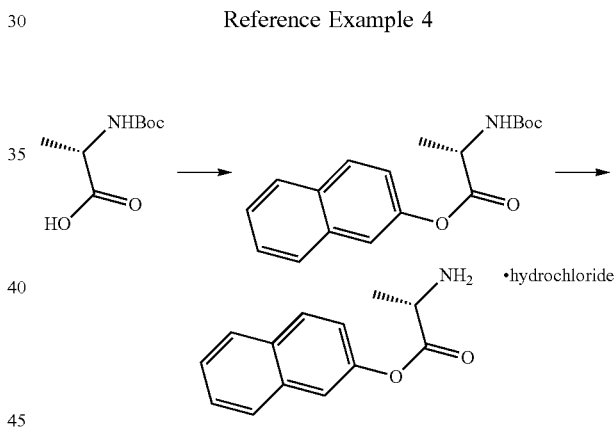

First Step

Triethylamine (2 mL) and HATU (4.87 g) were added to a mixture of N-(tert-butoxycarbonyl)-L-alanine (2.5 g), 2-naphthol (1.7 g), and methylene chloride (12 mL) which was then stirred overnight. Water was added to the reaction solution, extraction was carried out with ethyl acetate, the solvent was distilled off under reduced pressure, and then the obtained residue was purified by silica gel column chromatography (hexane:ethyl acetate=100:0 to 60:40) to give naphthalen-2-yl (tert-butoxycarbonyl)-L-alaninate (0.70 g).

MS (ESI m/z): 316 (M+H)
RT (min): 1.68

Second Step

A mixture of naphthalen-2-yl (tert-butoxycarbonyl)-L-alaninate (0.70 g) and a 4 M hydrochloric acid/cyclopentyl methyl ether solution (5 mL) was stirred at room temperature overnight. After distilling off the solvent under reduced pressure, ethyl acetate was added to the obtained residue and the resulting solid was collected by filtration to give naphthalen-2-yl L-alaninate hydrochloride (0.26 g) as a white solid.

MS (ESI m/z): 216 (M+H)
RT (min): 0.81

Reference Example 5-1

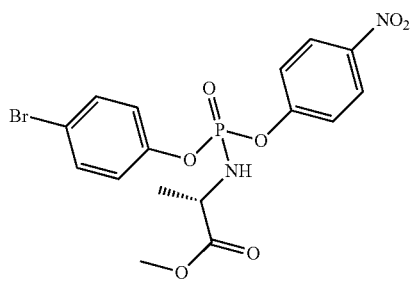 [SMILES: COC(=O)[C@H](C)NP(=O)(Oc1ccc(Br)cc1)Oc1ccc([N+](=O)[O-])cc1]

Under a nitrogen atmosphere, a mixture of 4-bromophenol (1.2 g), triethylamine (0.94 mL), and methylene chloride (15 mL) was added dropwise at −78° C. to a mixture of 4-nitrophenyl phosphorodichloridate (1.7 g) and methylene chloride (15 mL) which was then stirred at −78° C. for 30 minutes. A mixture of L-alanine methyl ester hydrochloride (0.94 g), triethylamine (1.9 mL), and methylene chloride (30 mL) was added dropwise at −78° C. to the reaction solution which was then stirred at −78° C. for 30 minutes and at room temperature for 1 hour. After distilling off the solvent under reduced pressure, methylene chloride (10 mL) was added to the obtained residue, and the resulting solid was filtered off. After distilling off the solvent under reduced pressure, the obtained residue was purified by silica gel column chromatography (hexane:ethyl acetate=90:10 to 0:100) to give ((4-bromophenoxy)(4-nitrophenoxy)phosphoryl)-L-alaninate (1.7 g) as a white solid.

MS (ESI m/z): 459, 461 (M+H)
RT (min): 1.56

Reference Example 5-2

The compounds in Table 1 were obtained in the same manner as in Reference Example 5-1.

TABLE 1

| Reference Example No. | R | Compound name | MS (ESI m/z) (M + H) | RT (min) |
|---|---|---|---|---|
| 5-2-1 | naphthalen-1-yl | Methyl ((naphthalen-1-yloxy)(4-nitrophenoxy)phosphoryl)-L-alaninate | 431 | 1.56 |
| 5-2-2 | 4-chlorophenyl | Methyl ((4-chlorophenoxy)(4-nitrophenoxy)phosphoryl)-L-alaninate | 415, 417 | 1.52 |
| 5-2-3 | 4-bromonaphthalen-1-yl | Methyl (((4-bromonaphthalen-1-yl)oxy)(4-nitrophenoxy)phosphoryl)-L-alaninate | 509, 511 | 1.75 |

TABLE 1-continued

| Reference Example No. | R | Compound name | MS (ESI m/z) (M + H) | RT (min) |
|---|---|---|---|---|
| 5-2-4 | | Methyl (((4-chloronaphthalen-1-yl) oxy)(4-nitrophenoxy) phosphoryl)-L-alaninate | 465 467 | 1.72 |
| 5-2-5 | | Ethyl ((4-nitrophenoxy)(phenoxy) phosphoryl)-L-alaninate | 395 | 1.49 |
| 5-2-6 | | Ethyl ((naphthalen-1-yloxy)(4-nitrophenoxy)phosphoryl)-L-alaninate | 445 | 1.65 |
| 5-2-7 | | Ethyl ((4-bromophenoxy)(4-nitrophenoxy)phosphoryl)-L-alaninate | 474 476 | 1.63 |
| 5-2-8 | | Ethyl ((4-chlorophenoxy) (4-nitrophenoxy) phosphoryl)-L-alaninate | 429 431 | 1.61 |

TABLE 1-continued

| Reference Example No. | R | Compound name | MS (ESI m/z) (M + H) | RT (min) |
|---|---|---|---|---|
| 5-2-9 | | Methyl ((2-bromophenoxy)(4-nitrophenoxy)phosphoryl)-L-alaninate | 459 461 | 1.52 |
| 5-2-10 | | Methyl ((2-chlorophenoxy)(4-nitrophenoxy)phosphoryl)-L-alaninate | 415 417 | 1.49 |
| 5-2-11 | | Methyl ((4-nitrophenoxy)(2-(pivaloylthio)ethoxy)phosphoryl)-L-alaninate | 449 | 1.56 |
| 5-2-12 | | Methyl ((2-isobutyrylthio)ethoxy)(4-nitrophenoxy)phosphoryl)-L-alaninate | 435 | 1.49 |
| 5-2-13 | | Methyl ((4-bromophenoxy)(4-nitrophenoxy)phosphoryl)glycinate | 445 447 | 1.48 |
| 5-2-14 | | Methyl ((4-bromophenoxy)(4-nitrophenoxy)phosphoryl)-D-alaninate | 459 461 | 1.55 |

TABLE 1-continued

| Reference Example No. | R | Compound name | MS (ESI m/z) (M + H) | RT (min) |
|---|---|---|---|---|
| 5-2-15 | | Dimethyl ((4-bromophenoxy)(4-nitrophenoxy)phosphoryl)-L-alaninate | 517 519 | 1.53 |
| 5-2-16 | | Methyl 2-(((4-bromophenoxy)(4-nitrophenoxy)phosphoryl) amino-2-methylpropanoate | 473 475 | 1.61 |
| 5-2-17 | | Methyl ((4-bromophenoxy)(4-nitrophenoxy)phosphoryl)-L-phenylalaninate | 535 537 | 1.75 |
| 5-2-18 | | Dipentyl ((4-bromophenoxy)(4-nitrophenoxy)phosphoryl)-L-aspartate | 629 631 | 2.14 |
| 5-2-19 | | Methyl ((4-bromophenoxy)(4-nitrophenoxy)phosphoryl)-L-leucinate | 501 503 | 1.77 |

TABLE 1-continued

[Structure: *—O-C6H4-NO2 (4-nitrophenoxy)]

| Reference Example No. | R | Compound name | MS (ESI m/z) (M + H) | RT (min) |
|---|---|---|---|---|
| 5-2-20 | [4-bromophenyl phosphoramidate with N-methyl-L-alanine methyl ester] | Methyl N-((4-bromophenoxy)(4-nitrophenoxy)phosphoryl)-N-methyl-L-alaninate | 473 475 | 1.70 |
| 5-2-21 | [4-bromophenyl phosphoramidate with L-alanine N-methylamide] | 4-bromophenyl (4-nitrophenyl)((S)-1-(methyl-amino)-1-oxopropan-2-yl) phosphoramidate | 458 460 | 1.31 |
| 5-2-22 | [4-chloro-2-fluorophenyl phosphoramidate with L-alanine methyl ester] | Methyl ((4-chloro-2-fluorophenoxy)(4-nitrophenoxy) phosphoryl)-L-alaninate | 433 435 | 1.56 |
| 5-2-23 | [3-bromophenyl phosphoramidate with L-alanine methyl ester] | Methyl ((3-bromophenoxy)(4-nitrophenoxy) phosphoryl)-L-alaninate | 459 461 | 1.55 |
| 5-2-24 | [4-bromophenyl phosphoramidate with L-alanine isobutyl ester] | Isobutyl ((4-bromophenoxy)(4-nitrophenoxy) phosphoryl)-L-alaninate | 501 503 | 1.80 |
| 5-2-25 | [4-bromophenyl phosphoramidate with L-alanine cyclobutyl ester] | Cyclobutyl ((4-bromophenoxy)(4-nitrophenoxy) phosphoryl)-L-alaninate | 500 502 | 1.75 |

TABLE 1-continued

Structure: 4-nitrophenyl group with O linkage at *

| Reference Example No. | R | Compound name | MS (ESI m/z) (M + H) | RT (min) |
|---|---|---|---|---|
| 5-2-26 | (4-bromophenyl)-O-P(=O)(CH3)-NH-CH(CH3)-C(=O)-O-(naphthalen-2-yl) structure | Naphthalen-2-yl ((4-bromophenoxy)(4-nitrophenoxy)phosphoryl)-L-alaninate | 571 573 | 1.86 |

Reference Example 6-1

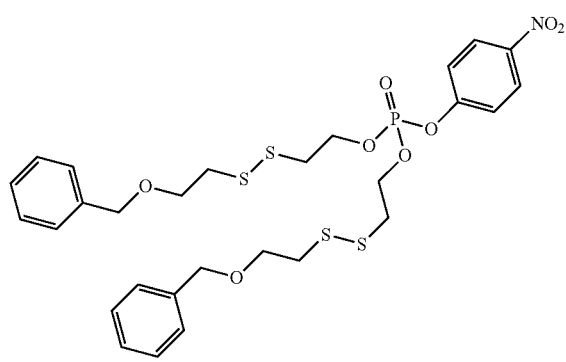 [SMILES: O=[N+]([O-])c1ccc(OP(=O)(OCCSSCCOCc2ccccc2)OCCSSCCOCc2ccccc2)cc1]

Under a nitrogen atmosphere, triethylamine (0.45 mL) was added to a mixture of 4-nitrophenyl phosphorodichloridate (0.16 g) and methylene chloride (2 mL) under ice-cooling, and then 2-((2-(benzyloxy)ethyl)disulfanyl)ethanol (0.39 g) and methylene chloride (2 mL) were added thereto, which was followed by stirring at room temperature for 1.5 hours. The reaction solution was purified by silica gel column chromatography (hexane:ethyl acetate=80:20 to 25:75) to give bis(2-((2-(benzyloxy)ethyl)disulfanyl)ethyl)(4-nitrophenyl)phosphate (0.33 g) as a colorless oil.

1H-NMR (CDCl$_3$) δ: 8.27-8.17 (m, 2H), 7.43-7.24 (m, 10H), 4.54 (s, 4H), 4.46-4.34 (m, 4H), 3.79-3.66 (m, 4H), 2.99-2.87 (m, 8H).

Reference Example 6-2

The compounds in Table 2 were obtained in the same manner as in Reference Example 6-1.

TABLE 2

Structure: 4-nitrophenyl group with O linkage at *

| Reference Example No. | R | Compound name | MS (ESI m/z) (M + H) | RT (min) |
|---|---|---|---|---|
| 6-2-1 | Bis(S-pivaloyl-2-mercaptoethyl) phosphate structure | Bis(S-pivaloyl-2-mercapto-ethan-1-yl)(4-nitrophenyl) phosphate | 508 | 1.96 |

TABLE 2-continued

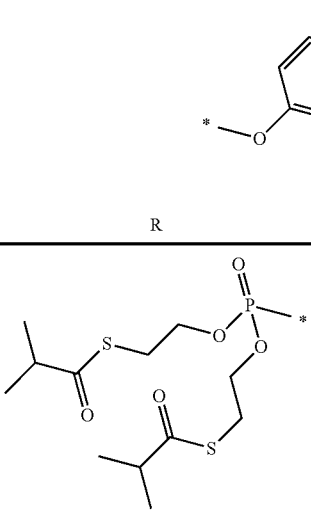

| Reference Example No. | R | Compound name | MS (ESI m/z) (M + H) | RT (min) |
|---|---|---|---|---|
| 6-2-2 | | Bis(S-isobutyroyl-2-mercapto-ethan-1-yl)(4-nitrophenyl) phosphate | 480 | 1.82 |

Reference Example 7-1

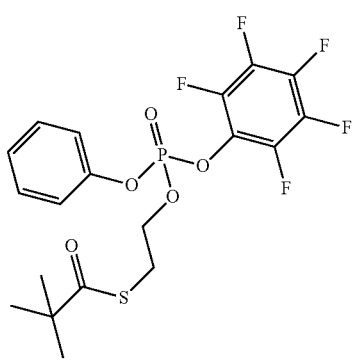 [SMILES: CC(C)(C)C(=O)SCCOP(=O)(Oc1ccccc1)Oc1c(F)c(F)c(F)c(F)c1F]

Under a nitrogen atmosphere, a mixture of perfluorophenol (0.62 g), triethylamine (0.47 mL), and methylene chloride (5 mL) was added dropwise to a mixture of phenyl phosphorodichloridate (0.5 mL) and methylene chloride (5 mL) at −78° C., which was followed by stirring at −78° C. for 1 hour. A mixture of S-(2-hydroxyethyl) 2,2-dimethylpropanethioate (0.54 g), triethylamine (0.94 mL), and methylene chloride (5 ml) was added dropwise to the reaction solution at −78° C., which was followed by stirring at −78° C. for 1.5 hours and then at room temperature for 40 minutes. After distilling off the solvent under reduced pressure, the obtained residue was purified by silica gel column chromatography (hexane:ethyl acetate=90:10 to 70:30) to give S-(2-(((perfluorophenoxy)(phenoxy)phosphoryl)oxy)ethyl) 2,2-dimethylpropanethioate (0.86 g) as a colorless oil.
MS (ESI m/z): 485 (M+H)
RT (min): 2.01

Reference Example 7-2

The compounds in Table 3 were obtained in the same manner as in Reference Example 7-1.

TABLE 3

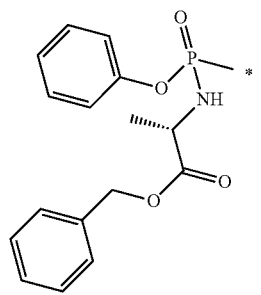 [SMILES: C[C@H](NP(C)(=O)Oc1ccccc1)C(=O)OCc1ccccc1]

| Reference Example No. | R | Compound name | MS (ESI m/z) (M + H) | RT (min) |
|---|---|---|---|---|
| 7-2-1 | | Benzyl ((perfluorophenoxy)(phenoxy) phosphoryl)-L-alaninate | 502 | 1.84 |

TABLE 3-continued

[R group header structure: pentafluorophenoxy]

| Reference Example No. | R | Compound name | MS (ESI m/z) (M + H) | RT (min) |
|---|---|---|---|---|
| 7-2-2 | [structure] | Isopropyl ((perfluorophenoxy)(phenoxy) phosphoryl)-L-alaninate | 454 | 1.79 |
| 7-2-3 | [structure] | Methyl ((perfluorophenoxy)(phenoxy) phosphoryl)-L-alaninate | 426 | 1.59 |
| 7-2-4 | [structure] | Isopropyl ((naphthalen-1-yloxy) (perfluorophenoxy)phosphoryl)-L-alaninate | 504 | 1.92 |

Reference Example 8

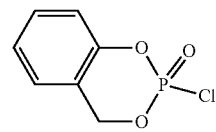

The following compound was obtained according to the method described in Chem. Eur. J. 2011, 17, 1649-1659.

2-chloro-4H-benzo[d][1,3,2]dioxaphosphinine 2-oxide
MS (ESI m/z): 205, 207 (M+H)
RT (min): 1.11

Reference Example 9

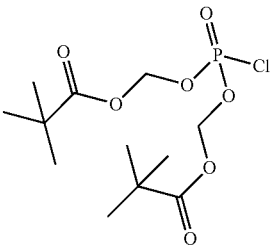 [SMILES: CC(C)(C)C(=O)OCOP(=O)(Cl)OCOC(=O)C(C)(C)C]

The following compound was obtained according to the method described in Org. Lett., Vol. 6, No. 10, 2004, 1555-1556.

((Chlorophosphoryl)bis(oxy))bis(methylene)bis(2,2-dimethylpropanoate)

Example 1-1

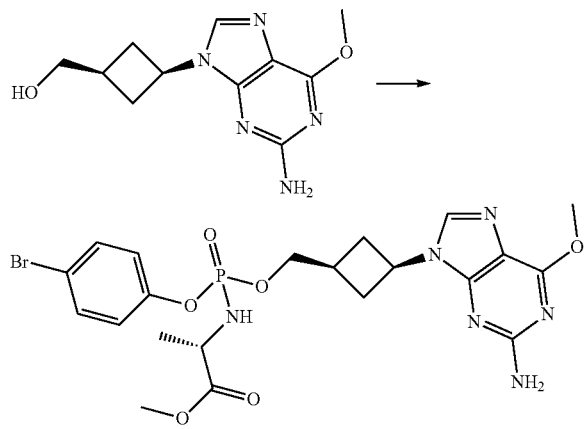

Under a nitrogen atmosphere, a 1.0 M tert-butyl magnesium chloride/tetrahydrofuran solution (0.25 mL) was added dropwise to a mixture of (cis-3-(2-amino-6-methoxy-9H-purin-9-yl)cyclobutyl)methanol (20 mg) and tetrahydrofuran (0.5 mL) which was then stirred at room temperature for 30 minutes. A mixture of (methyl ((4-bromophenoxy)(4-nitrophenoxy)phosphoryl)-L-alaninate (39 mg) and tetrahydrofuran (0.5 mL) was added to the reaction solution which was then stirred at room temperature for 16 hours. An aqueous saturated ammonium chloride solution was added to the reaction solution, which was followed by extraction with ethyl acetate and washing with an aqueous saturated sodium chloride solution. The solvent was distilled off under reduced pressure, and the obtained residue was purified by silica gel column chromatography (hexane:ethyl acetate=50:50 to 0:100, methanol:ethyl acetate=0:100 to 20:80) to give methyl (((cis-3-(2-amino-6-methoxy-9H-purin-9-yl)cyclobutyl)methoxy)(4-bromophenoxy)phosphoryl)-L-alaninate (23 mg) as a pale yellow solid.

$^1$H-NMR (MeOD) δ: 7.97-7.86 (m, 1H), 7.36-7.26 (m, 2H), 7.26-7.14 (m, 2H), 4.85-4.71 (m, 1H), 4.29-4.12 (m, 2H), 4.09-3.89 (m, 4H), 3.71-3.60 (m, 3H), 2.68-2.40 (m, 5H), 1.40-1.28 (m, 3H).

MS (ESI m/z): 569, 571 (M+H).

RT (min): 1.18

Example 1-2

The compounds in Table 4-1 to Table 4-4 were obtained in the same manner as in Example 1-1.

TABLE 4-1

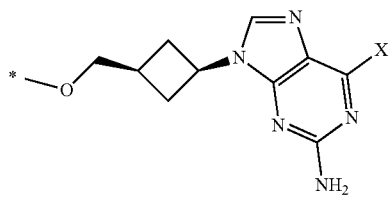

| Example No. | R | X | Compound name | $^1$H-NMR | MS (ESI m/z) (M + H) | RT (min) |
|---|---|---|---|---|---|---|
| 1-2-1 | (naphthalen-1-yloxy phosphoryl-L-alanine methyl ester structure) | OMe | Methyl (((cis-3-(2-amino-6-methoxy-9H-purin-9-yl)cyclobutyl) methoxy) (naphthalen-1-yloxy) phosphoryl)-L-alanin | $^1$H-NMR (CD$_3$OD) δ: 8.20-8.09 (m, 1H), 7.91-7.72 (m, 2H), 7.72-7.59 (m, 1H), 7.56-7.34 (m, 4H), 4.80-4.64 (m, 1H), 4.31-4.16 (m, 2H), 4.16-3.96 (m, 4H), 3.62 (s, 3H), 2.64-2.27 (m, 5H), 1.40-1.26 (m, 3H). | 541 | 1.18 |
| 1-2-2 | (4-chlorophenoxy phosphoryl-L-alanine methyl ester structure) | OMe | Methyl (((cis-3-(2-amino-6-methoxy-9H-purin-9-yl)cyclobutyl) methoxy)(4-chloro-phenoxy)phosphoryl)-L-alaninate | $^1$H-NMR (CD$_3$OD) δ: 7.96-7.88 (m, 1H), 7.37-7.26 (m, 2H), 7.25-7.14 (m, 2H), 4.85-4.73 (m, 1H), 4.28-4.13 (m, 2H), 4.08-3.89 (m, 4H), 3.70-3.60 (m 3H), 2.69-2.39 (m, 5H), 1.42-1.24 (m, 3H). | 525 527 | 1.15 |

TABLE 4-1-continued

| Example No. | R | X | Compound name | ¹H-NMR | MS (ESI m/z) (M + H) | RT (min) |
|---|---|---|---|---|---|---|
| 1-2-3 | (4-bromonaphthalen-1-yl structure) | OMe | Methyl (((cis-3-(2-amino-6-methoxy-9H-purin-9-yl)cyclobutyl)methoxy)((4-bromonaphthalen-1-yl)oxy)phosphoryl)-L-alaninate | ¹H-NMR (CDCl₃) δ: 8.28-8.10 (m, 2H), 7.75-7.54 (m, 4H), 7.49-7.41 (m, 1H), 4.99 (s, 2H), 4.80-4.66 (m, 1H), 4.36-4.27 (m, 2H), 4.21-4.04 (m, 4H), 3.85-3.60 (m, 4H), 2.69-2.47 (m, 5H), 1.46-1.33 (m, 3H). | 619 621 | 1.35 |
| 1-2-4 | (4-chloronaphthalen-1-yl structure) | OMe | Methyl (((cis-3-(2-amino-6-methoxy-9H-purin-9-yl)cyclobutyl)methoxy)((4-chloronaphthalen-1-yl)oxy)phosphoryl)-L-alaninate | ¹H-NMR (CDCl₃) δ: 8.27-8.22 (m, 1H), 8.17-8.12 (m, 1H), 7.67-7.55 (m, 3H), 7.49 (s, 2H), 4.98 (s, 2H), 4.80-4.65 (m, 1H), 4.36-4.25 (m, 2H), 4.20-4.04 (m, 4H), 3.82-3.62 (m, 4H), 2.66-2.47 (m, 5H), 1.41-1.33 (m, 3H). | 575 577 | 1.33 |
| 1-2-5 | (phenoxy structure) | OMe | Ethyl (((cis-3-(2-amino-6-methoxy-9H-purin-9-yl)cyclobutyl)methoxy)(phenoxy)phosphoryl)-L-alaninate | ¹H-NMR (CDCl₃) δ: 7.61-7.57 (m, 1H), 7.37-7.12 (m, 5H), 5.03-4.91 (m, 2H), 4.81-4.66 (m, 1H), 4.35-3.97 (m, 8H), 3.65-3.52 (m, 1H), 2.68-2.45 (m, 5H), 1.47-1.36 (m, 3H), 1.33-1.20 (m, 3H). | 505 | 1.11 |
| 1-2-6 | (naphthalen-1-yloxy structure) | OMe | Ethyl (((cis-3-(2-amino-6-methoxy-9H-purin-9-yl)cyclobutyl)methoxy)(naphthalen-1-yloxy)phosphoryl)-L-alaninate | ¹H-NMR (CDCl₃) δ: 8.17-8.09 (m, 1H), 7.87-7.81 (m, 1H), 7.70-7.63 (m, 1H), 7.57-7.48 (m, 4H), 7.43-7.35 (m, 1H), 5.01-4.91 (m, 2H), 4.76-4.40 (m, 1H), 4.36-4.22 (m, 2H), 4.19-4.00 (m, 6H), 3.78-3.59 (m, 1H), 2.60-2.43 (m, 5H), 1.45-1.33 (m, 3H), 1.30-1.14 (m, 3H). | 555 | 1.26 |
| 1-2-7 | (4-bromophenoxy structure) | OMe | Ethyl (((cis-3-(2-amino-6-methoxy-9H-purin-9-yl)cyclobutyl)methoxy)(4-bromophenoxy)phosphoryl)-L-alaninate | ¹H-NMR (CDCl₃) δ: 7.67-7.62 (m, 1H), 7.47-7.38 (m, 2H), 7.19-7.08 (m, 2H), 5.04-4.94 (m, 2H), 4.82-4.68 (m, 1H), 4.34-3.93 (m, 8H), 3.76-3.57 (m, 1H), 2.71-2.45 (m, 5H), 1.50-1.34 (m, 3H), 1.32-1.20 (m, 3H). | 583 585 | 1.26 |

TABLE 4-1-continued

| Example No. | R | X | Compound name | ¹H-NMR | MS (ESI m/z) (M + H) | RT (min) |
|---|---|---|---|---|---|---|
| 1-2-8 | (4-chlorophenoxy with ethyl L-alaninate phosphoryl group) | OMe | Ethyl (((cis-3-(2-amino-6-methoxy-9H-purin-9-yl)cyclobutyl)methoxy)(4-chlorophenoxy)phosphoryl)-L-alaninate | ¹H-NMR (CDCl₃) δ: 7.66-7.62 (m, 1H), 7.31-7.25 (m, 2H), 7.22-7.14 (m, 2H), 5.01-4.93 (m, 2H), 4.81-4.68 (m, 1H), 4.30-4.10 (m, 4H), 4.10-3.95 (m, 4H), 3.67-3.54 (m, 1H), 2.67-2.48 (m, 4H), 1.44-1.35 (m, 3H), 1.30-1.21 (m, 4H). | 539 541 | 1.24 |
| 1-2-9 | (2-bromophenoxy with methyl L-alaninate phosphoryl group) | OMe | Methyl (((cis-3-(2-amino-6-methoxy-9H-purin-9-yl)cyclobutyl)methoxy)(2-bromophenoxy)phosphoryl)-L-alaninate | ¹H-NMR (CDCl₃) δ: 7.64-7.49 (m, 3H), 7.32-7.23 (m, 1H), 7.07-7.00 (m, 1H), 5.02-4.91 (m, 2H), 4.80-4.67 (m, 1H), 4.36-4.04 (m, 6H), 3.77-3.64 (m, 4H), 2.67-2.42 (m, 5H), 1.47-1.34 (m, 3H). | 569 571 | 1.12 1.13 |
| 1-2-10 | (2-chlorophenoxy with methyl L-alaninate phosphoryl group) | OMe | Methyl (((cis-3-(2-amino-6-methoxy-9H-purin-9-yl)cyclobutyl)methoxy)(2-chlorophenoxy)phosphoryl)-L-alaninate | ¹H-NMR (CDCl₃) δ: 7.63-7.59 (m, 1H), 7.55-7.48 (m, 1H), 7.44-7.37 (m, 1H), 7.26-7.18 (m, 1H), 7.14-7.05 (m, 1H), 5.01-4.92 (m, 2H), 4.81-4.65 (m, 1H), 4.35-4.03 (m, 6H), 3.79-3.63 (m, 4H), 2.68-2.42 (m, 5H), 1.48-1.33 (m, 3H). | 525 527 | 1.10 1.11 |
| 1-2-11 | (2-(pivaloylthio)ethoxy with methyl L-alaninate phosphoryl group) | OMe | Methyl (((cis-3-(2-amino-6-methoxy-9H-purin-9-yl)cyclobutyl)methoxy)(2-(pivaloylthio)ethoxy)phosphoryl)-L-alaninate | 1H-NMR (CDCl3) δ: 7.71-7.68 (m, 1H), 5.09-4.95 (m, 2H), 4.83-4.69 (m, 1H), 4.25-3.91 (m, 8H), 3.80-3.71 (m, 3H), 3.53-3.37 (m, 1H), 3.24-3.09 (m, 2H), 2.72-2.47 (m, 5H), 1.49-1.38 (m, 3H), 1.32-1.20 (m, 9H). | 559 | 1.23 |

TABLE 4-2

| Example No. | R | X | Compound name | ¹H-NMR | MS (ESI m/z) (M + H) | RT (min) |
|---|---|---|---|---|---|---|
| 1-2-12 | (isobutyrylthio-ethyl/methyl L-alaninate phosphoramidate group) | OMe | Methyl (((cis-3-(2-amino-6-methoxy-9H-purin-9-yl)cyclobutyl)methoxy)(2-(isobutyrylthio)ethoxy)phosphoryl)-L-alaninate | ¹H-NMR (CDCl₃) δ: 7.72-7.68 (m, 1H), 5.01 (br s, 2H), 4.83-4.69 (m, 1H), 4.23-3.91 (m, 8H), 3.78-3.71 (m, 3H), 3.52-3.37 (m, 1H), 3.23-3.12 (m, 2H), 2.83-2.48 (m, 6H), 1.50-1.39 (m, 3H), 1.39-1.22 (m, 6H). | 545 | 1.14 |
| 1-2-13 | bis(S-isobutyroyl-2-mercaptoethyl)phosphate | OMe | (cis-3-(2-amino-6-methoxy-9H-purin-9-yl)cyclobutyl)methyl bis(S-isobutyroyl-2-mercaptoethan-1-yl)phosphate | ¹H-NMR (CDCl₃) δ: 7.68-7.64 (m, 1H), 5.07 (br s, 2H), 4.81-4.69 (m, 1H), 4.26-4.17 (m, 2H), 4.26-4.10 (m, 4H), 4.06 (s, 3H), 3.18 (t, 4H, J = 6.6 Hz), 2.82-2.50 (m, 7H), 1.19 (d, 12H, J = 6.6 Hz). | 590 | 1.46 |
| 1-2-14 | bis(2-((2-(benzyloxy)ethyl)disulfanyl)ethyl)phosphate | OMe | (cis-3-(2-amino-6-methoxy-9H-purin-9-yl)cyclobutyl)methyl bis(2-((2-(benzyloxy)ethyl)disulfanyl)ethyl)phosphate | ¹H-NMR (CD₃OD) δ: 7.89 (s, 1H), 7.36-7.13 (m, 10H), 4.84-4.69 (m, 1H), 4.54-4.42 (m, 4H), 4.35-4.11 (m, 6H), 4.02 (s, 3H), 3.77-3.60 (m, 4H), 3.03-2.79 (m, 8H), 2.65-2.45 (m, 5H). | 782 | 1.77 |
| 1-2-15 | bis(S-pivaloyl-2-mercaptoethyl)phosphate | OMe | (cis-3-(2-amino-6-methoxy-9H-purin-9-yl)cyclobutyl)methyl bis(S-pivaloyl-2-mercaptoethan-1-yl)phosphate | ¹H-NMR (CD₃OD) δ: 7.95 (s, 1H), 4.87-4.78 (m, 1H), 4.27-4.18 (m, 2H), 4.18-4.07 (m, 4H), 4.04 (s, 3H), 3.32-3.11 (m, 4H), 2.68-2.55 (m, 5H), 1.21 (s, 18H). | 618 | 1.60 |
| 1-2-16 | (4-bromophenoxy)/methyl L-alaninate phosphoramidate group | NMe₂ | Methyl (((cis-3-(2-amino-6-(dimethylamino)-9H-purin-9-yl)cyclobutyl)methoxy)(4-bromophenoxy)phosphoryl)-L-alaninate | ¹H-NMR (CD₃OD) δ: 7.84-7.78 (m, 1H), 7.52-7.43 (m, 2H), 7.21-7.11 (m, 2H), 4.82-4.69 (m, 1H), 4.26-4.14 (m, 2H), 4.04-3.90 (m, 1H), 3.71-3.62 (m, 3H), 3.41 (s, 6H), 2.68-2.31 (m, 5H), 1.41-1.31 (m, 3H). | 582 584 | 1.09 |

TABLE 4-2-continued

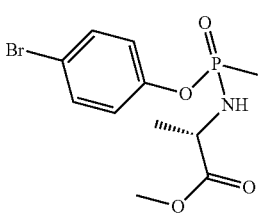

| Example No. | R | X | Compound name | ¹H-NMR | MS (ESI m/z) (M + H) | RT (min) |
|---|---|---|---|---|---|---|
| 1-2-17 | 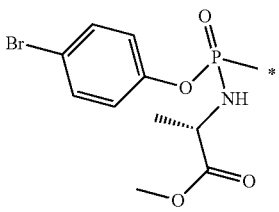 | SMe | Methyl (((cis-3-(2-amino-6-(methylthio)-9H-purin-9-yl) cyclobutyl) methoxy)(4-bromophenoxy) phosphoryl)-L-alaninate | ¹H-NMR (CD₃OD) δ: 8.01-7.95 (m, 1H), 7.51-7.43 (m, 2H), 7.20-7.10 (m, 2H), 4.86-4.77 (m, 1H), 4.29-4.15 (m, 2H), 4.03-3.90 (m, 1H), 3.71-3.63 (m, 3H), 2.68-2.43 (m, 8H), 1.39-1.31 (m, 3H). | 585 587 | 1.28 |
| 1-2-18 | 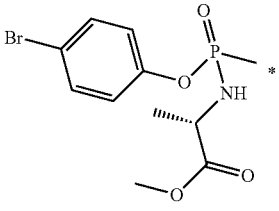 | NHMe | Methyl (((cis-3-(2-amino-6-(methylamino)-9H-purin-9-yl) cyclobutyl) methoxy)(4-bromo-phenoxy) phosphoryl)-L-alaninate | ¹H-NMR (CD₃OD) δ: 7.87-7.80 (m, 1H), 7.51-7.43 (m, 2H), 7.20-7.11 (m, 2H), 4.81-4.70 (m, 1H), 4.29-4.14 (m, 2H), 4.04-3.89 (m, 1H), 3.70-3.65 (m, 3H), 3.07-3.01 (m, 3H), 2.69-2.29 (m, 5H), 1.42-1.31 (m, 3H). | 568 570 | 1.04 |
| 1-2-19 | 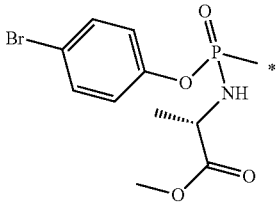 | OEt | Methyl (((cis-3-(2-amino-6-ethoxy-9H-purin-9-yl) cyclobutyl) methoxy)(4-bromophenoxy) phosphoryl)-L-alaninate | ¹H-NMR (CD₃OD) δ: 7.96-7.89 (m, 1H), 7.51-7.43 (m, 2H), 7.19-7.11 (m, 2H), 4.84-4.75 (m, 1H), 4.53 (q, 2H, J = 7.0 Hz), 4.27-4.16 (m, 2H), 4.03-3.90 (m, 1H), 3.70-3.65 (m, 3H), 2.69-2.35 (m, 5H), 1.43 (t, 3H, J = 7.0 Hz), 1.38-1.32 (m, 3H). | 583 585 | 1.25 |
| 1-2-20 | 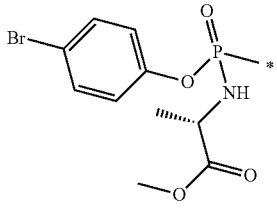 | NH₂ | Methyl ((4-bromophenoxy) ((cis-3-(2,6-diamino-9H-purin-9-yl)cyclobutyl) methoxy) phosphoryl)-L-alaninate | ¹H-NMR (CD₃OD) δ: 7.92-7.85 (m, 1H), 7.51-7.44 (m, 2H), 7.21-7.11 (m, 2H), 4.83-4.71 (m, 2H), 4.27-4.15 (m, 2H), 4.03-3.91 (m, 1H), 3.71-3.65 (m, 3H), 2.69-2.38 (m, 5H), 1.39-1.31 (m, 3H). | 554 556 | 1.02 |
| 1-2-21 |  | Cl | Methyl (((cis-3-(2-amino-6-chloro-9H-purin-9-yl) cyclobutyl) methoxy)(4-bromophenoxy) phosphoryl)-L-alaninate | ¹H-NMR (CD₃OD) δ: 8.17-8.13 (m, 1H), 7.51-7.44 (m, 2H), 7.20-7.11 (m, 2H), 4.91-4.84 (m, 1H), 4.28-4.16 (m, 2H), 4.03-3.90 (m, 1H), 3.69-3.66 (m, 3H), 2.67-2.54 (m, 5H), 1.39-1.31 (m, 3H). | 573 575 | 1.25 |

TABLE 4-2-continued

| Example No. | R | X | Compound name | ¹H-NMR | MS (ESI m/z) (M + H) | RT (min) |
|---|---|---|---|---|---|---|
| 1-2-22 | Br-phenyl-O-P(=O)(Me)-NH-CH2-C(=O)-OMe | OMe | Methyl (((cis-3-(2-amino-6-methoxy-9H-purin-9-yl)cyclobutyl)methoxy)(4-bromophenoxy)phosphoryl)glycinate | ¹H-NMR (CDCl₃) δ: 7.66 (s, 1H), 7.47-7.40 (m, 2H), 7.18-7.10 (m, 2H), 4.99 (s, 2H), 4.82-4.69 (m, 1H), 4.33-4.24 (m, 2H), 4.07 (s, 3H), 3.86-3.73 (m, 5H), 3.68-3.57 (m, 1H), 2.68-2.48 (m, 5H). | 555 557 | 1.11 |

TABLE 4-3

| Example No. | R | X | Compound name | ¹H-NMR | MS (ESI m/z) (M + H) | RT (min) |
|---|---|---|---|---|---|---|
| 1-2-23 | Br-phenyl-O-P(=O)(Me)-NH-CH(Me)-C(=O)-OMe | OMe | Methyl (((cis-3-(2-amino-6-methoxy-9H-purin-9-yl)cyclobutyl)methoxy)(4-bromophenoxy)phosphoryl)-D-alaninate | ¹H-NMR (CDCl₃) δ: 7.68-7.64 (m, 1H), 7.49-7.39 (m, 2H), 7.18-7.08 (m, 2H), 5.01 (s, 2H), 4.84-4.69 (m, 1H), 4.35-3.98 (m, 6H), 3.78-3.62 (m, 4H), 2.72-2.45 (m, 5H), 1.47-1.35 (m, 3H). | 569 571 | 1.17 |
| 1-2-24 | Br-phenyl-O-P(=O)(Me)-NH-CH(CH2CO2Me)-C(=O)-OMe | OMe | Dimethyl (((cis-3-(2-amino-6-methoxy-9H-purin-9-yl)cyclobutyl)methoxy)(4-bromophenoxy)phosphoryl)-L-aspartate | ¹H-NMR (CDCl₃) δ: 7.69-7.63 (m, 1H), 7.47-7.39 (m, 2H), 7.17-7.08 (m, 2H), 5.01 (s, 2H), 4.82-4.67 (m, 1H), 4.36-4.19 (m, 3H), 4.12-3.98 (m, 4H), 3.74-3.71 (m, 3H), 3.66-3.63 (m, 3H), 3.01-2.44 (m, 7H). | 627 629 | 1.17 |
| 1-2-25 | Br-phenyl-O-P(=O)(Me)-NH-C(Me)2-C(=O)-OMe | OMe | Methyl 2-((((cis-3-(2-amino-6-methoxy-9H-purin-9-yl)cyclobutyl)methoxy)(4-bromophenoxy)phosphoryl)amino)-2-methylpropanoate | ¹H-NMR (CDCl₃) δ: 7.64 (s, 1H), 7.47-7.38 (m, 2H), 7.18-7.10 (m, 2H), 4.98 (s, 2H), 4.83-4.68 (m, 1H), 4.28-4.21 (m, 2H), 4.07 (s, 3H), 4.01-3.94 (m, 1H), 3.73 (s, 3H), 2.68-2.47 (m, 5H), 1.56 (s, 3H), 1.54 (s, 3H). | 583 585 | 1.23 |

TABLE 4-3-continued

| Example No. | R | X | Compound name | ¹H-NMR | MS (ESI m/z) (M + H) | RT (min) |
|---|---|---|---|---|---|---|
| 1-2-26 | Br-phenyl-O-P(=O)(NH-CH(CH2Ph)-C(=O)-OMe)-* | OMe | Methyl (((cis-3-(2-amino-6-methoxy-9H-purin-9-yl)cyclobutyl) methoxy) (4-bromophenoxy) phosphoryl)-L-phenylalaninate | ¹H-NMR (CDCl₃) δ: 7.63 (s, 1H), 7.44-7.34 (m, 2H), 7.29-7.18 (m, 3H), 7.13-6.99 (m, 4H), 4.96 (s, 2H), 4.79-4.65 (m, 1H), 4.32-4.19 (m, 1H), 4.17-3.81 (m, 5H), 3.71-3.65 (m, 3H), 3.47-3.33 (m, 1H), 3.10-2.92 (m, 2H), 2.64-2.34 (m, 5H). | 645 647 | 1.40 |
| 1-2-27 | Br-phenyl-O-P(=O)(NH-CH(CH2C(=O)OPentyl)-C(=O)-OPentyl)-* | OMe | Dipentyl (((cis-3-(2-amino-6-methoxy-9H-purin-9-yl)cyclobutyl) methoxy) (4-bromophenoxy) phosphoryl)-L-aspartate | ¹H-NMR (CDCl₃) δ: 7.68-7.61 (m, 1H), 7.46-7.39 (m, 2H), 7.17-7.08 (m, 2H), 4.99 (s, 2H), 4.82-4.67 (m, 1H), 4.34-3.95 (m, 11H), 3.00-2.46 (m, 7H), 1.71-1.50 (m, 4H), 1.39-1.19 (m, 8H), 0.93-0.84 (m, 6H). | 739 741 | 1.84 |
| 1-2-28 | Br-phenyl-O-P(=O)(NH-CH(iBu)-C(=O)-OMe)-* | OMe | Methyl (((cis-3-(2-amino-6-methoxy-9H-purin-9-yl)cyclobutyl) methoxy)(4-bromophenoxy) phosphoryl)-L-leucinate | ¹H-NMR (CDCl₃) δ: 7.68-7.62 (m, 1H), 7.47-7.39 (m, 2H), 7.17-7.08 (m, 2H), 4.99 (s, 2H), 4.82-4.67 (m, 1H), 4.31-4.18 (m, 2H), 4.07 (s, 3H), 4.05-3.88 (m, 1H), 3.71-3.65 (m, 3H), 3.47-3.30 (m, 1H), 2.67-2.45 (m, 5H), 1.76-1.41 (m, 3H), 0.93-0.84 (m, 6H). | 611 613 | 1.42 |
| 1-2-29 | Br-phenyl-O-P(=O)(N(Me)-CH(Me)-C(=O)-OMe)-* | OMe | Methyl N-(((cis-3-(2-amino-6-methoxy-9H-purin-9-yl)cyclobutyl) methoxy) (4-bromophenoxy) phosphoryl)-N-methyl-L-alaninate | ¹H-NMR (CDCl₃) δ: 7.77-7.66 (m, 1H), 7.47-7.39 (m, 2H), 7.18-7.19 (m, 2H), 4.99-4.91 (m, 2H), 4.87-4.71 (m, 1H), 4.62-4.37 (m, 1H), 4.33-4.13 (m, 2H), 4.07 (s, 3H), 3.72-3.62 (m, 3H), 2.78-2.45 (m, 8H), 1.42-1.27 (m, 3H). | 583 585 | 1.28 1.30 |
| 1-2-30 | Br-phenyl-O-P(=O)(NH-CH(Me)-C(=O)-NHMe)-* | OMe | (cis-3-(2-amino-6-methoxy-9H-purin-9-yl)cyclobutyl) methyl)(4-bromophenyl)((S)-1-(methylamino)-1-oxopropan-2-yl) phosphoramidate | ¹H-NMR (CDCl₃) δ: 7.64-7.60 (m, 1H), 7.48-7.39 (m, 2H), 7.16-7.09 (m, 2H), 6.19-6.10 (m, 1H), 5.07-4.96 (m, 2H), 4.80-4.68 (m, 1H), 4.29-4.23 (m, 2H), 4.07 (s, 3H), 3.92-3.78 (m, 1H), 3.64-3.54 (m, 1H), 2.77-2.72 (m, 3H), 2.68-2.48 (m, 5H), 1.40-1.34 (m, 3H). | 568 570 | 0.98 |

TABLE 4-3-continued

| Example No. | R | X | Compound name | ¹H-NMR | MS (ESI m/z) (M + H) | RT (min) |
|---|---|---|---|---|---|---|
| 1-2-31 | 4-chloro-2-fluorophenoxy with methyl phosphoryl, methyl L-alaninate | OMe | Methyl (((cis-3-(2-amino-6-methoxy-9H-purin-9-yl)cyclobutyl)methoxy)(4-chloro-2-fluorophenoxy)phosphoryl)-L-alaninate | ¹H-NMR (CDCl₃) δ: 7.68-7.65 (m, 1H), 7.43-7.34 (m, 1H), 7.19-7.12 (m, 1H), 7.11-7.05 (m, 1H), 4.97 (s, 2H), 4.83-4.69 (m, 1H), 4.34-4.23 (m, 2H), 4.17-4.00 (m, 4H), 3.76-3.61 (m, 4H), 2.69-2.47 (m, 5H), 1.45-1.36 (m, 3H). | 543 545 | 1.18 |
| 1-2-32 | 3-bromophenoxy with methyl phosphoryl, methyl L-alaninate | OMe | Methyl (((cis-3-(2-amino-6-methoxy-9H-purin-9-yl)cyclobutyl)methoxy)(3-bromophenoxy)phosphoryl)-L-alaninate | ¹H-NMR (CDCl₃) δ: 7.64-7.60 (m, 1H), 7.44-7.39 (m, 1H), 7.32-7.26 (m, 1H), 7.23-7.14 (m, 2H), 4.98 (s, 2H), 4.82-4.68 (m, 1H), 4.34-4.16 (m, 2H), 4.15-3.96 (m, 4H), 3.75-3.71 (m, 3H), 3.70-3.55 (m, 1H), 2.68-2.48 (m, 5H), 1.44-1.37 (m, 3H). | 569 571 | 1.17 |
| 1-2-33 | 4-bromophenoxy with methyl phosphoryl, isobutyl L-alaninate | OMe | Isobutyl (((cis-3-(2-amino-6-methoxy-9H-purin-9-yl)cyclobutyl)methoxy)(4-bromophenoxy)phosphoryl)-L-alaninate | ¹H-NMR (CDCl₃) δ: 7.65-7.62 (m, 1H), 7.46-7.38 (m, 2H), 7.16-7.08 (m, 2H), 4.98 (br s, 2H), 4.80-4.67 (m, 1H), 4.31-4.20 (m, 2H), 4.10-3.96 (m, 4H), 3.95-3.81 (m, 2H), 3.69-3.55 (m, 1H), 2.67-2.49 (m, 5H), 1.98-1.83 (m, 1H), 1.45-1.36 (m, 3H), 0.90 (d, 6H, J = 6.6 Hz). | 611 613 | 1.44 |

TABLE 4-4

| Example No. | R | X | Compound name | ¹H-NMR | MS (ESI m/z) (M + H) | RT (min) |
|---|---|---|---|---|---|---|
| 1-2-34 | 4-bromophenoxy with methyl phosphoryl, cyclobutyl L-alaninate | OMe | Cyclobutyl (((cis-3-(2-amino-6-methoxy-9H-purin-9-yl)cyclobutyl)methoxy)(4-bromophenoxy)phosphoryl)-L-alaninate | ¹H-NMR (CDCl₃) δ: 7.65 (s, 1H), 7.45-7.28 (m, 2H), 7.16-7.08 (m, 2H), 5.03-4.92 (m, 3H), 4.81-4.68 (m, 1H), 4.30-4.19 (m, 2H), 4.07 (s, 3H), 4.04-3.92 (m, 1H), 3.68-3.54 (m, 1H), 2.67-2.48 (m, 5H), 2.39-2.26 (m, 2H), 2.09-1.95 (m, 2H), 1.86-1.66 (m, 2H), 1.42-1.85 (m, 3H). | 609 611 | 1.38 |

TABLE 4-4-continued

| Example No. | R | X | Compound name | ¹H-NMR | MS (ESI m/z) (M + H) | RT (min) |
|---|---|---|---|---|---|---|
| 1-2-35 | Br—⟨phenyl⟩—O—P(=O)(CH₃)—O—*—NH—CH(CH₃)—C(=O)—O—(naphthalen-2-yl) | OMe | Naphthalen-2-yl (((cis-3-(2-amino-6-methoxy-9H-purin-9-yl)cyclobutyl) methoxy)(4-bromophenoxy) phosphoryl)-L-alaninate | ¹H-NMR (CDCl₃) δ: 7.88-7.72 (m, 3H), 7.65-7.59 (m, 1H), 7.54-7.41 (m, 5H), 7.24-7.08 (m, 3H), 5.02-4.90 (m, 2H), 4.80-4.67 (m, 1H), 4.40-4.26 (m, 3H), 4.08-4.03 (m, 3H), 3.82-3.55 (m, 1H), 2.70-2.54 (m, 5H), 1.74-1.59 (m, 3H). | 681 683 | 1.53 |

Example 2-1

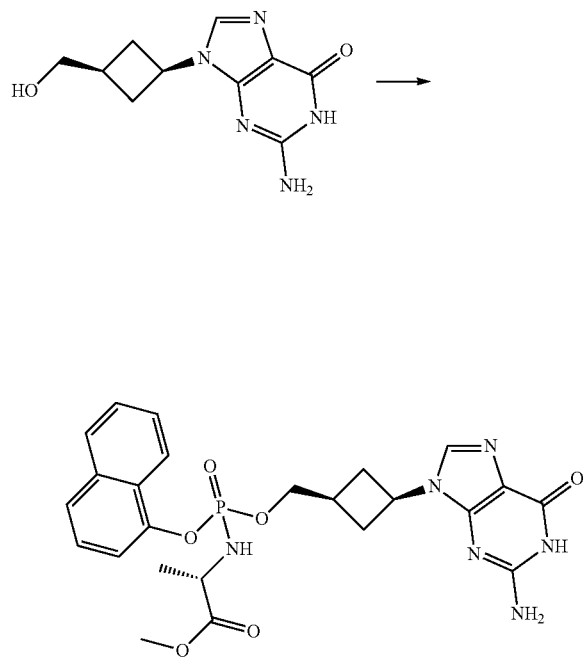

Under a nitrogen atmosphere, a 1.0 M tert-butyl magnesium chloride/tetrahydrofuran solution (0.20 mL) was added dropwise to a mixture of 2-amino-9-(cis-3-(hydroxymethyl)cyclobutyl)-1,9-dihydro-6H-purin-6-one (20 mg), N,N-dimethylformamide (0.5 mL), and tetrahydrofuran (2.0 mL) which was then stirred at room temperature for 1 hour. A mixture of methyl ((naphthalen-1-yloxy)(4-nitrophenoxy)phosphoryl)-L-alaninate (36 mg) and tetrahydrofuran (0.5 mL) was added to the reaction solution which was then stirred at room temperature for 18 hours. An aqueous saturated ammonium chloride solution was added to the reaction solution, which was followed by extraction with ethyl acetate and washing with an aqueous saturated sodium chloride solution. The solvent was distilled off under reduced pressure, and the obtained residue was purified by silica gel column chromatography (hexane:ethyl acetate=50:50 to 0:100, methanol:ethyl acetate=0:100 to 20:80) to give methyl (((cis-3-(2-amino-6-oxo-1,6-dihydro-9H-purin-9-yl)cyclobutyl)methoxy)(naphthalen-1-yloxy) phosphoryl)-L-alaninate (8.5 mg) as a pale yellow solid.

¹H-NMR (MeOD) δ: 8.20-8.11 (m, 1H), 7.90-7.80 (m, 1H), 7.75-7.59 (m, 2H), 7.59-7.33 (m, 2H), 4.77-4.62 (m, 1H), 4.29-4.14 (m, 2H), 4.14-3.97 (m, 1H), 3.67-3.56 (m, 3H), 2.59-2.28 (m, 5H), 1.40-1.26 (m, 3H).

MS (ESI m/z): 527 (M+H)
RT (min): 1.05

Example 2-2

The compounds in Table 5 were obtained in the same manner as in Example 2-1.

TABLE 5

| Example No. | R | X | Compound name | ¹H-NMR | MS (ESI m/z) (M + H) | RT (min) |
|---|---|---|---|---|---|---|
| 2-2-1 | 4-Cl-phenyl alaninate structure | OH | Methyl (((cis-3-(2-amino-6-hydroxy-9H-purin-9-yl)cyclobutyl) methoxy)(4-chlorophenoxy) phosphoryl)-L-alaninate | ¹H-NMR (MeOD) δ: 7.84-7.76 (m, 1H), 7.37-7.27 (m, 2H), 7.27-7.14 (m, 2H), 4.81-4.69 (m, 1H), 4.27-4.14 (m, 2H), 4.03-3.89 (m, 1H), 3.70-3.62 (m, 3H), 2.67-2.37 (m, 5H), 1.43-1.25 (m, 3H). | 511 513 | 1.02 |
| 2-2-2 | 4-Br-phenyl alaninate structure | OH | Methyl (((cis-3-(2-amino-6-hydroxy-9H-purin-9-yl)cyclobutyl) methoxy)(4-bromophenoxy) phosphoryl)-L-alaninate | ¹H-NMR (MeOD) δ: 7.85-7.75 (m, 1H), 7.51-7.42 (m, 2H), 7.20-7.07 (m, 2H), 4.82-4.67 (m, 1H), 4.29-4.11 (m, 2H), 4.02-3.86 (m, 1H), 3.72-3.63 (m, 3H), 2.66-2.37 (m, 5H), 1.40-1.29 (m, 3H). | 555 557 | 1.04 |
| 2-2-3 | 4-Br-phenyl alaninate structure | SH | Methyl (((cis-3-(2-amino-6-mercapto-9H-purin-9-yl)cyclobutyl)methoxy) (4-bromophenoxy) phosphoryl)-L-alaninate | 1H-NMR (MeOD) δ: 7.96-7.92 (m, 1H), 7.51-7.43 (m, 2H), 7.19-7.11 (m, 2H), 4.82-4.70 (m, 1H), 4.28-4.14 (m, 2H), 4.03-3.89 (m, 1H), 3.70-3.64 (m, 3H), 2.67-2.40 (m, 5H), 1.38-1.31 (m, 3H). | 571 573 | 1.11 |

Example 3-1

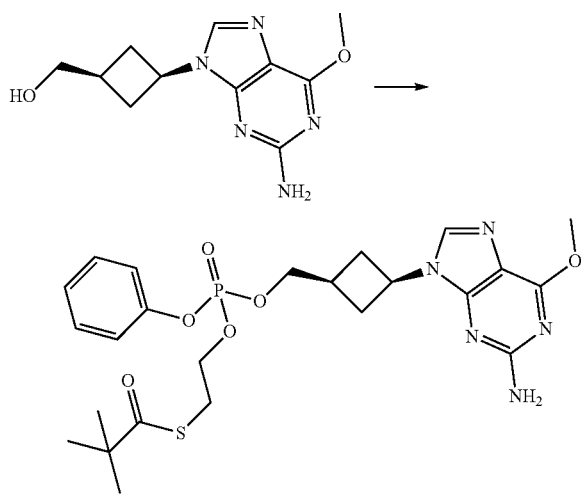

Under a nitrogen atmosphere, a 1.0 M tert-butyl magnesium chloride/tetrahydrofuran solution (0.25 mL) was added dropwise to a mixture of (cis-3-(2-amino-6-methoxy-9H-purin-9-yl)cyclobutyl)methanol (20 mg) and tetrahydrofuran (0.2 mL) which was then stirred at room temperature for 20 minutes. A mixture of S-(2-(((perfluorophenoxy) (phenoxy)phosphoryl)oxy)ethyl) 2,2-dimethylpropanethioate (30 mg) and tetrahydrofuran (0.15 mL) was added to the reaction solution which was then stirred at room temperature for 11 hours. An aqueous saturated ammonium chloride solution was added to the reaction solution, which was followed by extraction with ethyl acetate and washing with an aqueous saturated sodium chloride solution. The solvent was distilled off under reduced pressure, and the obtained residue was purified by silica gel column chromatography (hexane:ethyl acetate=50:50 to 0:100, methanol:ethyl acetate=0:100 to 5:95) to give S-(2-((((cis-3-(2-amino-6-methoxy-9H-purin-9-yl)cyclobutyl)methoxy)(phenoxy) phosphoryl) oxy)ethyl)2,2-dimethylpropanethioate (7.0 mg) as a pale yellow solid.

¹H-NMR (MeOD) δ: 7.89-7.84 (m, 1H), 7.42-7.30 (m, 2H), 7.27-7.17 (m, 3H), 4.86-4.74 (m, 1H), 4.40-4.15 (m, 4H), 4.04 (s, 3H), 3.22-3.11 (m, 2H), 2.65-2.49 (m, 5H), 1.19 (s, 9H).
MS (ESI m/z): 550 (M+H)
RT (min): 1.45

Example 3-2

The compounds in Table 6 were obtained in the same manner as in Example 3-1.

TABLE 6

| Example No. | R | X | Compound name | ¹H-NMR | MS (ESI m/z) (M + H) | RT (min) |
|---|---|---|---|---|---|---|
| 3-2-1 | | OMe | Benzyl (((cis-3-(2-amino-6-methoxy-9H-purin-9-yl)cyclobutyl)methoxy)(phenoxy)phosphoryl)-L-alaninate | ¹H NMR (MeOD) δ: 7.99-7.80 (m, 1H), 7.36-7.08 (m, 10H), 5.13-5.06 (m, 2H), 4.82-4.65 (m, 1H), 4.18-3.94 (m, 6H), 2.59-2.30 (m, 5H), 1.40-1.27 (m, 3H). | 567 | 1.30 |
| 3-2-2 | | OMe | Methyl (((cis-3-(2-amino-6-methoxy-9H-purin-9-yl)cyclobutyl)methoxy)(phenoxy)phosphoryl)-L-alaninate | 1H NMR (MeOD) δ: 7.92-7.84 (m, 1H), 7.38-7.09 (m, 5H), 4.90-4.72 (m, 1H), 4.26-4.07 (m, 2H), 4.07-3.89 (m, 4H), 3.69-3.60 (m, 3H), 2.66-2.37 (m, 5H), 1.41-1.25 (m, 3H). | 491 | 1.03 |
| 3-2-3 | | NHcycloPr | Isopropyl (((cis-3-(2-amino-6-(cyclopropyl-amino)-9H-purin-9-yl)cyclobutyl)methoxy)(phenoxy)phosphoryl)-L-alaninate | ¹H NMR (MeOD) δ: 7.78 (s, 1H), 7.37-7.11 (m, 5H), 5.00-4.92 (m, 1H), 4.81-4.67 (m, 1H), 4.20-4.14 (m, 2H), 3.97-3.83 (m, 1H), 2.95-2.85 (m, 1H), 2.64-2.49 (m, 3H), 2.49-2.33 (m, 2H), 1.38-1.31 (m, 3H), 1.24-1.17 (m, 6H), 0.88-0.80 (m, 2H), 0.64-0.56 (m, 2H). | 544 | 1.09 |
| 3-2-4 | | OMe | Isopropyl (((cis-3-(2-amino-6-methoxy-9H-purin-9-yl)cyclobutyl)methoxy)(phenoxy)phosphoryl)-L-alaninate | ¹H NMR (MeOD) δ: 7.88 (s, 1H), 7.38-7.11 (m, 5H), 5.10-4.92 (m, 1H), 4.84-4.72 (m, 1H), 4.22-4.15 (m, 2H), 4.04 (s, 3H), 3.97-3.84 (m, 1H), 2.64-2.40 (m, 5H), 1.38-1.31 (m, 3H), 1.25-1.17 (m, 6H). | 519 | 1.08 |

TABLE 6-continued

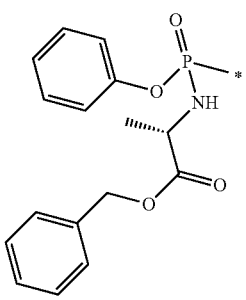 [SMILES: C[C@H](NP(C)(=O)Oc1ccccc1)C(=O)OCc1ccccc1]

| Example No. | R | X | Compound name | ¹H-NMR | MS (ESI m/z) (M + H) | RT (min) |
|---|---|---|---|---|---|---|
| 3-2-5 | 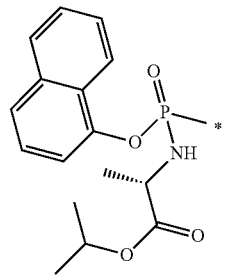 | OH | Benzyl (((cis-3-(2-amino-6-hydroxy-9H-purin-9-yl)cyclobutyl) methoxy) (phenoxy) phosphoryl)-L-alaninate | ¹H NMR (MeOD) δ: 7.77-7.72 (m, 1H), 7.38-7.10 (m, 10H), 5.17-5.08 (m, 2H), 4.79-4.63 (m, 1H), 4.18-3.93 (m, 3H), 2.58-2.28 (m, 5H), 1.39-1.30 (m, 3H). | 553 | 1.19 |
| 3-2-6 | 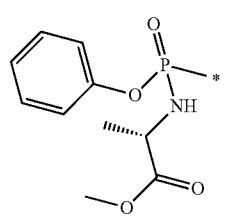 | OH | Isopropyl (((cis-3-(2-amino-6-hydroxy-9H-purin-9-yl)cyclobutyl) methoxy) (naphthalen-1-yloxy) phosphoryl)-L-alaninate | ¹H NMR (MeOD) δ: 8.20-8.13 (m, 1H), 7.89-7.82 (m, 1H), 7.72-7.61 (m, 2H), 7.55-7.36 (m, 4H), 5.00-4.83 (m, 1H), 4.74-4.61 (m, 1H), 4.28-4.17 (m, 2H), 4.05-3.93 (m, 1H), 2.57-2.27 (m 5H), 1.38-1.30 (m, 3H), 1.22-1.14 (m, 6H). | 555 | 1.19 1.18 |
| 3-2-7 | 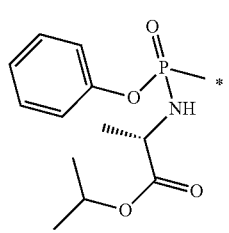 | OH | Methyl (((cis-3-(2-amino-6-hydroxy-9H-purin-9-yl)cyclobutyl) methoxy) (phenoxy)phosphoryl)-L-alaninate | ¹H NMR (MeOD) δ: 7.76-7.69 (m, 1H), 7.38-7.13 (m, 5H), 4.81-4.67 (m, 1H), 4.20-4.12 (m, 2H), 4.03-3.93 (m, 1H), 3.67 (s, 3H), 2.63-2.33 (m, 5H), 1.39-1.33 (m, 3H). | 477 | 0.90 |
| 3-2-8 | | OH | Isopropyl (((cis-3-(2-amino-6-hydroxy-9H-purin-9-yl)cyclobutyl) methoxy)(phenoxy) phosphoryl)-L-alaninate | ¹H NMR (MeOD) δ: 7.75 (s, 1H), 7.38-7.12 (m, 5H), 5.01-4.85 (m, 1H), 4.81-4.68 (m, 1H), 4.21-4.13 (m, 2H), 3.96-3.84 (m, 1H), 2.61-2.37 (m, 5H), 1.38-1.31 (m, 3H), 1.25-1.18 (m, 6H). | 505 | 1.06 |

Example 4-1

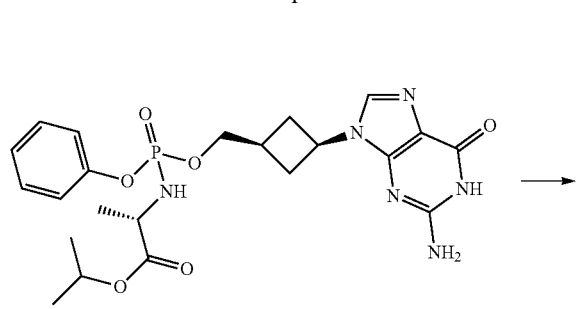

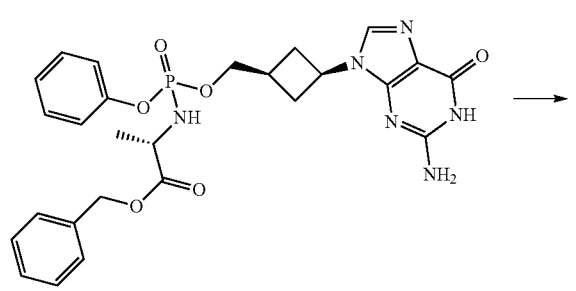

Acetyl chloride (28 μL) was added to a mixture of isopropyl (((cis-3-(2-amino-6-oxo-1,6-dihydro-9H-purin-9-yl)cyclobutyl)methoxy)(phenoxy)phosphoryl)-L-alaninate (7 mg) and pyridine (0.1 mL) which was then stirred at room temperature for 5 hours. Water was added to the reaction solution, followed by extraction with ethyl acetate, the solvent was distilled off under reduced pressure, and the obtained residue was purified by silica gel column chromatography (methanol:ethyl acetate=0:100 to 20:80) to give isopropyl (((cis-3-(2-acetamido-6-oxo-1,6-dihydro-9H-purin-9-yl)cyclobutyl)methoxy)(phenoxy)phosphoryl)-L-alaninate (4.4 mg) as a pale yellow solid.

¹H-NMR (MeOD) δ: 7.96 (s, 1H), 7.38-7.12 (m, 5H), 5.01-4.78 (m, 2H), 4.23-4.17 (m, 2H), 3.97-3.84 (m, 1H), 2.63-2.51 (m, 5H), 2.22 (s, 3H), 1.38-1.31 (m, 3H), 1.25-1.18 (m, 6H).

MS (ESI m/z): 547 (M+H)

RT (min): 1.20

Example 4-2

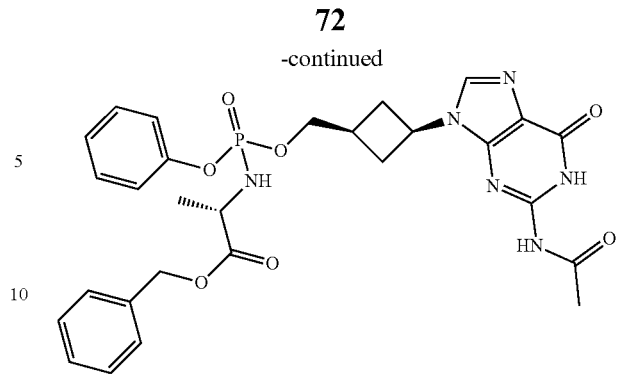

The following compound was obtained in the same manner as in Example 4-1.

Benzyl (((cis-3-(2-acetamido-6-oxo-1,6-dihydro-9H-purin-9-yl)cyclobutyl)methoxy)(phenoxy)phosphoryl)-L-alaninate ¹H-NMR (MeOD) δ: 7.97-7.92 (m, 1H), 7.39-7.11 (m, 10H), 5.16-5.07 (m, 2H), 4.86-4.75 (m, 1H), 4.24-3.94 (m, 3H), 2.62-2.38 (m, 5H), 2.24-2.18 (m, 3H), 1.40-1.31 (m, 3H).

MS (ESI m/z): 595 (M+H)

RT (min): 1.30

Example 5-1

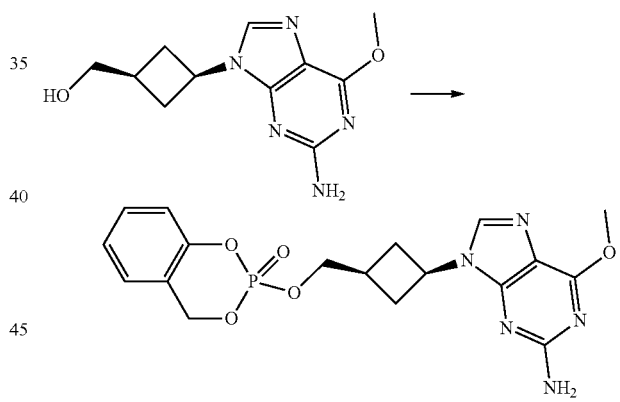

Under a nitrogen atmosphere, (cis-3-(2-amino-6-methoxy-9H-purin-9-yl)cyclobutyl)methanol (20 mg) and N-methylimidazole (38 μL) were added to a mixture of 2-chloro-4H-benzo[d][1,3,2]dioxaphosphinine 2-oxide (49 mg) and acetonitrile (1.0 mL) which was then stirred at room temperature for 1 hour. The reaction solution was purified by silica gel column chromatography (hexane:ethyl acetate=70:30 to 0:100, methanol:ethyl acetate=0:100 to 15:85) to give 2-((cis-3-(2-amino-6-methoxy-9H-purin-9-yl)cyclobutyl)methoxy)-4H-benzo[d][1,3,2] dioxaphosphinine 2-oxide (16 mg) as a pale yellow solid.

¹H-NMR (CDCl₃) δ: 7.56 (s, 1H), 7.36-7.29 (m, 1H), 7.18-7.05 (m, 3H), 5.48-5.31 (m, 2H), 4.99 (s, 2H), 4.84-4.66 (m, 1H), 4.43-4.31 (m, 2H), 4.06 (s, 3H), 2.67-2.51 (m, 5H).

MS (ESI m/z): 418 (M+H)

RT (min): 0.97

Example 5-2

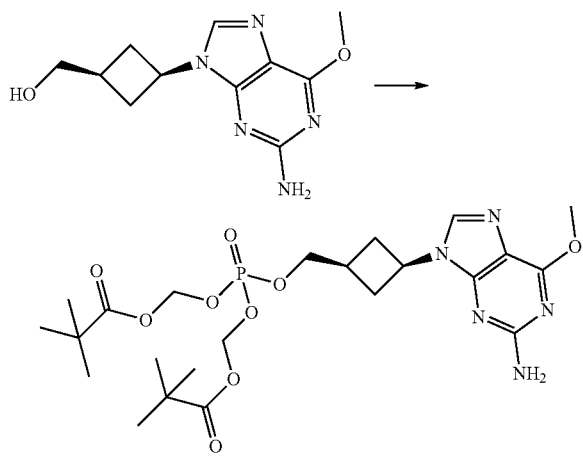

The following compound was obtained in the same manner as in Example 5-1.

(cis-3-(2-Amino-6-methoxy-9H-purin-9-yl)cyclobutyl)methylbis(pivaloyloxymethyl) phosphate $^1$H-NMR (CDCl$_3$) δ: 7.64 (s, 1H), 5.72-5.63 (m, 4H), 5.04 (s, 2H), 4.78-4.68 (m, 1H), 4.28-4.22 (m, 2H), 4.07 (s, 3H), 2.75-2.50 (m, 5H), 1.23 (s, 18H).

MS (ESI m/z): 558 (M+H)

RT (min): 1.42

Example 6

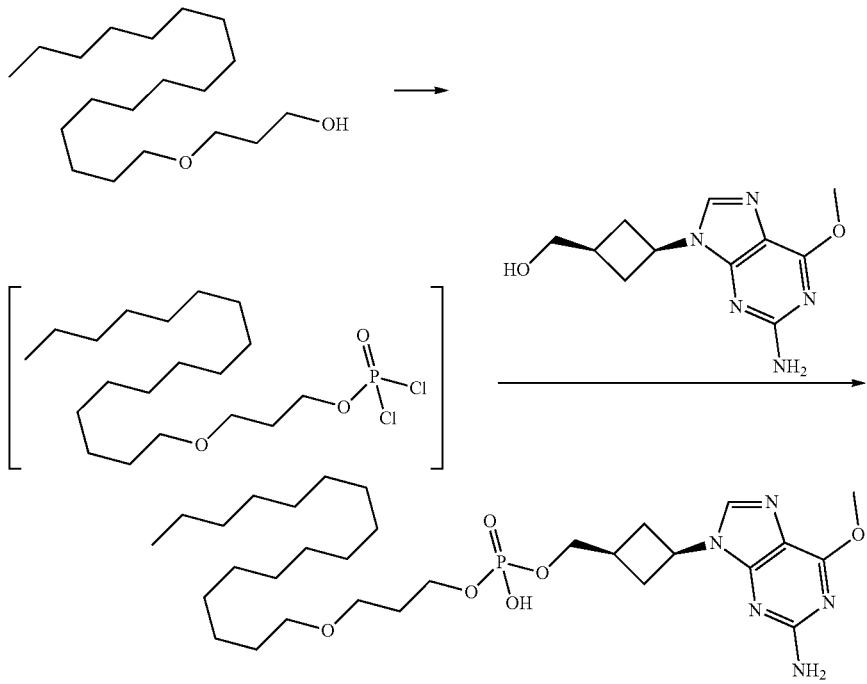

Under a nitrogen atmosphere, a mixture of 3-(hexadecyloxy)propan-1-ol (36 mg) and tetrahydrofuran (0.2 mL) was slowly added dropwise to a mixture of phosphorus oxychloride (11 μL), triethylamine (34 μL), and tetrahydrofuran (0.5 mL) under ice-cooling, which was followed by stirring at room temperature for 30 minutes. (cis-3-(2-Amino-6-methoxy-9H-purin-9-yl)cyclobutyl)methanol (10 mg) was added to the reaction solution which was then stirred at room temperature for 12 hours. Water (0.10 mL) and a 2 M aqueous sodium hydroxide solution (50 μL) were added to the reaction solution which was then stirred at room temperature for 15 minutes. The reaction mixture was purified by diol silica gel column chromatography (hexane:ethyl acetate=80:20 to 0:100, methanol: ethyl acetate=0:100 to 40:60) to give (cis-3-(2-amino-6)-methoxy-9H-purin-9-yl)cyclobutyl)methyl (3-(hexadecyloxy)propyl)hydrogen phosphate (6.3 mg) as a pale yellow solid.

$^1$H-NMR (CDCl$_3$) δ: 7.77 (s, 1H), 4.79-4.64 (m, 1H), 4.08-3.90 (m, 5H), 3.54-3.41 (m, 2H), 3.39-3.30 (m, 2H), 3.11-3.00 (m, 2H), 2.74-2.39 (m, 5H), 1.96-1.82 (m, 2H), 1.57-1.41 (m, 2H), 1.35-1.14 (m, 26H), 0.88 (t, 3H, J=6.6 Hz).

MS (ESI m/z): 612 (M+H)

RT (min): 2.37

Example 7

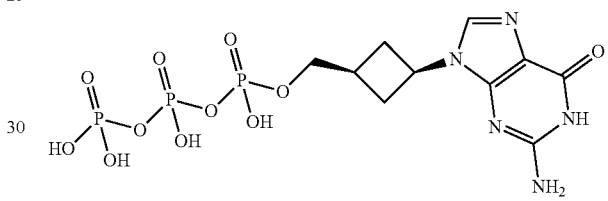

The following compound was obtained according to the method described in Nucleosides Nucleotides Nucleic Acids. 2006; 25 (4-6): 539-51.

(cis-3-(2-Amino-6-oxo-1,6-dihydro-9H-purin-9-yl)cyclobutyl)methyl tetrahydrogen triphosphate Examples 8-1-1 and 8-1-2

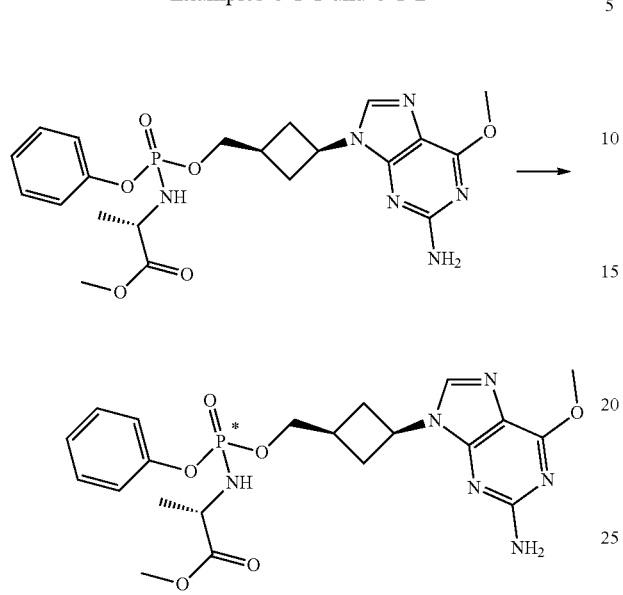

Methyl (((cis-3-(2-amino-6-methoxy-9H-purin-9-yl)cyclobutyl)methoxy)(phenoxy)phosphoryl)-L-alaninate obtained in Example 3-2-2 was subjected to chiral resolution by supercritical fluid chromatography to give optically active substance A and optically active substance B.

Example 8-1-1 (Optically Active Substance A)

$^1$H-NMR (CDCl$_3$) δ: 7.59 (s, 1H), 7.38-7.12 (m, 5H), 4.96 (br s, 2H), 4.82-4.67 (m, 1H), 4.34-4.18 (m, 2H), 4.18-4.04 (m, 4H), 3.71 (s, 3H), 3.61-3.48 (m, 1H), 2.70-2.48 (m, 5H), 1.39 (d, 3H, J=7.3 Hz).

MS (ESI m/z): 491 (M+H)

RT (min): 1.01

Example 8-1-2 (Optically Active Substance B)

$^1$H-NMR (CDCl$_3$) δ: 7.59 (s, 1H), 7.38-7.12 (m, 5H), 4.95 (br s, 2H), 4.82-4.66 (m, 1H), 4.33-4.14 (m, 2H), 4.14-3.97 (m, 4H), 3.72 (s, 3H), 3.65-3.52 (m, 1H), 2.68-2.45 (m, 5H), 1.40 (d, 3H, J=6.6 Hz).

MS (ESI m/z): 491 (M+H)

RT (min): 1.02

[Conditions for Supercritical Fluid Chromatography]
Column: CHIRALPAK IC (manufactured by Daicel Chemical Industries, Ltd.)
Mobile phase: carbon dioxide/methanol (volume ratio: 70/30)
Flow rate: 30 mL/min
Detection wavelength: 280 nm
Temperature: 40° C.
Retention time: 8.67 min (optically active substance A), 13.49 min (optically active substance B)

Examples 8-2-1 and 8-2-2

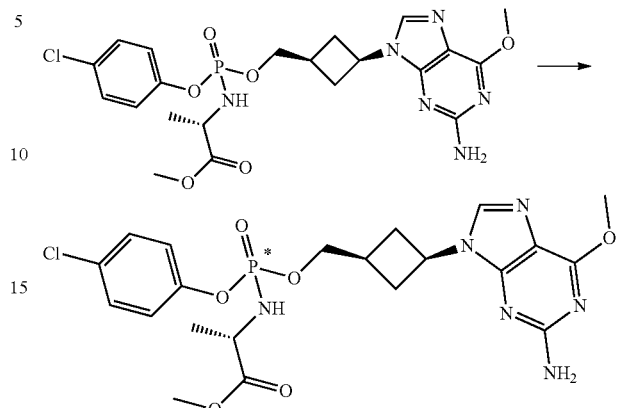

Methyl (((cis-3-(2-amino-6-methoxy-9H-purin-9-yl)cyclobutyl)methoxy)(4-chlorophenoxy)phosphoryl)-L-alaninate obtained in Example 1-2-2 was subjected to chiral resolution by supercritical fluid chromatography to give optically active substance A and optically active substance B.

Example 8-2-1 (Optically Active Substance A)

$^1$H-NMR (CDCl$_3$) δ: 7.65 (s, 1H), 7.32-7.24 (m, 2H), 7.21-7.14 (m, 2H), 4.97 (br s, 2H), 4.83-4.68 (m, 1H), 4.31-4.22 (m, 2H), 4.13-4.02 (m, 4H), 3.71 (s, 3H), 3.62-3.50 (m, 1H), 2.67-2.52 (m, 5H), 1.39 (d, 3H, J=7.3 Hz).

MS (ESI m/z): 525, 527 (M+H)

RT (min): 1.14

Example 8-2-2 (Optically Active Substance B)

$^1$H-NMR (CDCl$_3$) δ: 7.64 (s, 1H), 7.34-7.24 (m, 2H), 7.23-7.15 (m, 2H), 4.96 (s, 2H), 4.82-4.67 (m, 1H), 4.31-4.18 (m, 2H), 4.12-3.98 (m, 4H), 3.72 (s, 3H), 3.66-3.55 (m, 1H), 2.67-2.49 (m, 5H), 1.40 (d, 3H, J=7.3 Hz).

MS (ESI m/z): 525, 527 (M+H)

RT (min): 1.15

[Conditions for Supercritical Fluid Chromatography]
Column: CHIRALPAK IC (manufactured by Daicel Chemical Industries, Ltd.)
Mobile phase: carbon dioxide/methanol (volume ratio: 70/30)
Flow rate: 30 mL/min
Detection wavelength: 280 nm
Temperature: 40° C.
Retention time: 7.99 min (optically active substance A), 13.02 min (optically active substance B)

Comparative Example 1 (Reference Example 2-3)

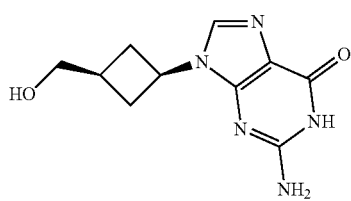 [SMILES: Nc1nc2c(ncn2[C@H]2C[C@@H](CO)C2)c(=O)[nH]1]

2-Amino-9-(cis-3-(hydroxymethyl)cyclobutyl)-1,9-dihydro-6H-purin-6-one

Test Example 1: Evaluation of Anti-Adenovirus Activity

A system in which CRL-11516 cells (available from ATCC) were infected with adenovirus type 6 (hereinafter, referred to as ADV6) was constructed, and a test for evaluating the anti-adenovirus activity of the compound according to the embodiment of the present invention and the compound of Comparative Example was carried out using the system. The test for evaluating the anti-adenovirus activity was carried out according to the method described below.

CRL-11516 cells were added to a 96-well plate at a cell density of $1 \times 10^4$ cells/well and cultured at 37° C. for 24 hours. After the culture was completed, the cell culture liquid was removed, and a serial dilution (100 µL) of the compound according to the embodiment of the present invention or the compound of Comparative Example was added. ADV6 (corresponding to $50TCID_{50}$) was added thereto, followed by culturing at 37° C. for 48 hours.

After the culture was completed, the infected cells were stained using Adeno-X Rapid Titer Kit (manufactured by Takara Bio Inc.). 100% methanol was added thereto and the cells were fixed at −20° C. for 10 minutes. The plate was washed three times with phosphate buffered saline (hereinafter, referred to as PBS) and then Mouse Anti-Hexon Antibody was added thereto, followed by incubation at 37° C. for 1 hour. After the incubation was completed, the plate was washed three times with PBS, and Rat Anti-Mouse Antibody was added thereto, followed by incubation at 37° C. for 1 hour. After the incubation was completed, a mixed staining solution of Stable Peroxidase Buffer:DAB Substrate=10:1 was added thereto, followed by incubation at room temperature for 10 minutes for staining of the cells.

The number of dark brown-stained cells was counted under a microscope, and the concentration of the test drug that reduces the dark brown-stained cells by 50% was defined as $EC_{50}$. $EC_{50}$ values were calculated for the triplicate test results, and a mean value and a standard deviation thereof were determined. The results are shown in Table 7 below.

TABLE 7

| Evaluation standards | |
|---|---|
| | Anti-AdV activity $EC_{50}$ (µmol/L) |
| Example No. | |
| 1-1 | +++ |
| 1-2-1 | ++ |
| 1-2-2 | +++ |
| 1-2-15 | + |
| 3-1 | + |
| 3-2-1 | ++ |
| 3-2-2 | ++ |
| 3-2-4 | + |

TABLE 7-continued

| Evaluation standards | |
|---|---|
| | Anti-AdV activity $EC_{50}$ (µmol/L) |
| 8-2-1 | +++ |
| 8-2-2 | ++ |
| Comparative Example No. | |
| 1 | − |

Evaluation standards
+++: $0.1\ \mu M > EC_{50}$
++: $1\ \mu M > EC_{50} \geq 0.1\ \mu M$
+: $10\ \mu M > EC_{50} \geq 1\ \mu M$
−: $IC_{50} \geq 10\ \mu M$ The compound according to the embodiment of the present invention had an excellent anti-adenovirus activity.

Test Example 2: Evaluation of ADV DNA Polymerase Inhibitory Activity

Recombinant ADV DNA polymerase was constructed, and a test for evaluating the DNA polymerase inhibitory activity of the compound described in Example 7 was carried out. The test for evaluating the DNA polymerase inhibitory activity was carried out according to the method described below.

1) Purification of Recombinant ADV DNA Polymerase

Full-length human adenovirus 19 DNA polymerase (AFA46720.1) was totally synthesized as a cDNA optimized for insect cell expression, a His tag sequence was added to the C-terminus thereof, and then the resulting construct was inserted into pFastBac™ 1 (available from Invitrogen Corporation).

A bacmid was constructed by introducing the above vector into MAX Efficiency (registered trademark) DH10Bac™ competent cells (available from Invitrogen Corporation). It was confirmed by sequencing that the constructed bacmid contained the full-length human adenovirus 19 DNA polymerase.

Sf9 cells were transfected with the bacmid using Cellfectin II (available from Invitrogen Corporation). The culture supernatant containing recombinant baculoviruses was recovered after 7 days, and an operation of infecting Sf9 cells with baculoviruses was repeated twice to obtain a sufficient amount of baculoviruses for protein expression. The baculovirus titer was measured using BacPAK™ Baculovirus Rapid Titer Kit (manufactured by Takara Bio Inc.).

$0.8 \times 10^6$ cells/mL of Sf9 cells were infected with baculoviruses in Grace's Insect medium (manufactured by Gibco Corporation) supplemented with 10% fetal bovine serum (hereinafter, referred to as FBS, manufactured by Gibco Corporation) and 0.1% F-68 (manufactured by Gibco Corporation), such that the multiplicity of infection was about 0.3. After 3 days, Sf9 cells were recovered and the cell pellet was frozen at −80° C.

The frozen cell pellet was suspended in a cell lysis solution (50 mM sodium phosphate buffer (pH 7.0), 10% glycerol, 300 mM sodium chloride, 1% Triton (registered trademark) X-100, cOmplete™ EDTA-free Protease Inhibitor Cocktail (manufactured by F. Hoffmann-La Roche AG)) which was then allowed to stand on ice for 15 minutes. After vortexing for 30 seconds, centrifugation was carried out at 15,000 rpm to obtain a supernatant containing human adenovirus 19 DNA polymerase.

The supernatant containing human adenovirus 19 DNA polymerase was added to TALON (registered trademark) Superflow Metal Affinity Resin (manufactured by Takara Bio Inc.) which was then stirred at 4° C. for 2.5 hours with a rotator. The TALON (registered trademark) Superflow Metal Affinity Resin was washed five times with a wash solution 1 (10 mM imidazole, 50 mM sodium phosphate buffer (pH 7.0), 10% glycerol, 300 mM sodium chloride) and three times with a wash solution 2 (25 mM imidazole, 50 mM sodium phosphate buffer (pH 7.0), 10% glycerol, 300 mM sodium chloride). Then, an eluate (50 mM and 100 mM imidazole, 50 mM sodium phosphate buffer (pH 7.0), 10% glycerol, 300 mM sodium chloride) was added to the TALON (registered trademark) Superflow Metal Affinity Resin to elute the human adenovirus 19 DNA polymerase. The eluate was concentrated with Amicon Ultra-15 Centrifugal Filter Units, MWCO 50K (manufactured by MilliporeSigma Corporation), and then replaced with stock buffer (50 mM sodium phosphate buffer (pH 7.0), 10% glycerol, 300 mM sodium chloride) by a dialysis method using Slide-A-Lyzer MINI Dialysis Devices, 20K MWCO (manufactured by Thermo Fisher Scientific Inc.) prior to use for testing. The concentration of human adenovirus 19 DNA polymerase was measured using Pierce™ BCA Protein Assay Kit.

2) Test for Evaluating ADV DNA Polymerase Inhibitory Activity 1.5 μM primer oligo DNA (IRDye800-5'-GTAAAACGACGGCCAGT-3') (SEQ ID NO: 1) and 1 μM template oligo DNA (5'-CCGGGGATCCTCTAGAGTCGACCTGCAGG-CATGCAAGCTTGGCACTGGCCGTCG TTTTA-CAACGTCGTGA-3') (SEQ ID NO: 2) were incubated in annealing buffer (10 mM Tris-HCl buffer (pH 8.0), 1 mM ethylenediaminetetraacetic acid (hereinafter, referred to as EDTA), 50 mM sodium chloride) at 95° C. for 5 minutes, and then the temperature was gradually returned to room temperature for annealing.

Human adenovirus 19 DNA polymerase, primer oligo DNA/template oligo DNA, dNTPs (manufactured by Nippon Gene Co., Ltd.), and the compound described in Example 7 were diluted in assay buffer (50 mM Tris-HCl buffer (pH 7.5), 1 mM dithiothreitol, 4% glycerol, 5 mM magnesium chloride, 0.1% bovine serum albumin).

40 nM human adenovirus 19 DNA polymerase (5 μL), the compound (5 μL) at a concentration four times the final concentration and described in Example 7, and 40 μM dNTPs (5 μL) were mixed and incubated at 37° C. for 5 minutes.

120 nM/80 nM primer oligo DNA/template oligo DNA (5 μL) was added to start an enzymatic reaction. After the enzymatic reaction at 37° C. for 10 minutes, 20 μL of 2× sample buffer (98% formamide, 10 mM EDTA, 0.2% bromophenol blue) was added to stop the reaction.

After incubating at 70° C. for 10 minutes, a part of the reaction solution was applied to Novex TBE-Urea gels, 15%, 15 well (manufactured by Thermo Fisher Scientific Inc.), and DNA was separated by electrophoresis. The extension of the primer oligo DNA by the DNA polymerase activity was evaluated by detecting IRDye800 with Odyssey (manufactured by LI-COR, Inc.). The results are shown in FIG. 1.

The compound according to the embodiment of the present invention had an excellent inhibitory activity on the DNA extension reaction by ADV DNA polymerase.

The compound represented by General Formula [1] or a salt thereof according to an aspect of the present invention is useful as an anti-adenoviral agent. The compound represented by General Formula [1] or a salt thereof according to the aspect of the present invention is useful as an agent for treating adenovirus.

[Sequence Listing]

International Application 18F01188W1 JP19029448_44. app under the Patent Cooperation Treaty.

What is claimed is:

1. A method for suppressing adenovirus, comprising:
administering a compound represented by General Formula [1] or a salt thereof:

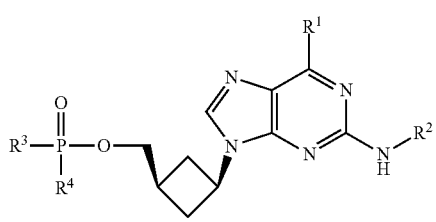

in the formula,
R¹ represents —OCH₃;
R² represents a hydrogen atom or an amino protecting group;
R³ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, or an amino group which may be substituted; and
R⁴ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or a hydroxyl group which may be protected; or
R³ and R⁴, together with a phosphorus atom to which R³ and R⁴ are bonded, may be combined to form a 5- to 10-membered nitrogen- and phosphorus-containing heterocyclic ring which may be substituted, a 5- to 10-membered oxygen- and phosphorus-containing heterocyclic ring which may be substituted, or a 5- to 10-membered nitrogen-, oxygen-, and phosphorus-containing heterocyclic ring which may be substituted.

2. The method according to claim 1,
wherein R² is a hydrogen atom; or the salt thereof.

3. The method according to claim 1,
wherein R³ is a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, or an amino group which may be substituted with one or more substituents selected from Substituent group A; or the salt thereof, Substituent group A:
a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; a $C_{1-6}$ alkoxycarbonyloxy group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B, Substituent group B:
a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an ar-$C_{1-6}$ alkoxycarbonyl group; an aryl group; an aryloxy group; a heterocyclic oxy group which may be substituted with one or more substituents selected from a hydroxyl group and a hydroxymethyl group; an ar-$C_{1-6}$ alkoxy group; and an acyloxy group.

4. The method according to claim 3,
wherein R³ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, or an amino group which may be substituted with one or more substituents selected from Substituent group A; or the salt thereof.

5. The method according to claim 3,
wherein R³ is a $C_{1-20}$ alkoxy group which may be substituted with one or more substituents selected from Substituent group A, a $C_{1-20}$ alkylthio group which may be substituted with one or more substituents selected from Substituent group A, or an aryloxy group which may be substituted with one or more substituents selected from Substituent group A; or the salt thereof.

6. The method according to claim 1,
wherein $R^4$ is a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or a hydroxyl group which may be protected; or the salt thereof, Substituent group A:
a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; a $C_{1-6}$ alkoxycarbonyloxy group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B, Substituent group B:
a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an ar-$C_{1-6}$ alkoxycarbonyl group; an aryl group; an aryloxy group; a heterocyclic oxy group which may be substituted with one or more substituents selected from a hydroxyl group and a hydroxymethyl group; an ar-$C_{1-6}$ alkoxy group; and an acyloxy group.

7. The method according to claim 6,
wherein $R^4$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected; or the salt thereof.

8. The method according to claim 6,
wherein $R^4$ is a $C_{1-20}$ alkoxy group which may be substituted with one or more substituents selected from Substituent group A, an amino group which may be substituted with one or more substituents selected from Substituent group A, or a hydroxyl group which may be protected; or the salt thereof.

9. The method according to claim 1,
wherein a ring formed by combining $R^3$ and $R^4$ together with a phosphorus atom to which $R^3$ and $R^4$ are bonded is a 5- to 10-membered oxygen- and phosphorus-containing heterocyclic ring which may be substituted; or the salt thereof.

10. The method according to claim 1, wherein the compound is selected from methyl (((cis-3-(2-amino-6-methoxy-9H-purin-9-yl)cyclobutyl)methoxy)(phenoxy) phosphoryl)-L-alaninate, methyl (((cis-3-(2-amino-6-methoxy-9H-purin-9-yl) cyclobutyl)methoxy)(naphthalen-1-yloxy) phosphoryl)-L-alaninate, methyl (((cis-3-(2-amino-6-methoxy-9H-purin-9-yl) cyclobutyl)methoxy)(4-chlorophenoxy) phosphoryl)-L-alaninate, methyl (((cis-3-(2-amino-6-methoxy-9H-purin-9-yl) cyclobutyl)methoxy) (4-bromophenoxy) phosphoryl)-L-alaninate, ethyl (((cis-3-(2-amino-6-methoxy-9H-purin-9-yl) cyclobutyl)methoxy) (4-bromophenoxy) phosphoryl)-L-alaninate, ethyl (((cis-3-(2-amino-6-methoxy-9H-purin-9-yl) cyclobutyl)methoxy) (4-chlorophenoxy) phosphoryl)-L-alaninate, methyl (((cis-3-(2-amino-6-methoxy-9H-purin-9-yl) cyclobutyl) methoxy)(2-bromophenoxy) phosphoryl)-L-alaninate, methyl (((cis-3-(2-amino-6-methoxy-9H-purin-9-yl) cyclobutyl)methoxy)(2-chlorophenoxy) phosphoryl)-L-alaninate, methyl (((cis-3-(2-amino-6-methoxy-9H-purin-9-yl) cyclobutyl) methoxy)(2-(pivaloylthio) ethoxy) phosphoryl)-L-alaninate, methyl (((cis-3-(2-amino-6-ethoxy-9H-purin-9-yl) cyclobutyl)methoxy)(4-bromophenoxy) phosphoryl)-L-alaninate, methyl 2-((((cis-3-(2-amino-6-methoxy-9H-purin-9-yl) cyclobutyl)methoxy)(4-bromophenoxy) phosphoryl) amino)-2-methylpropanoate, (cis-3-(2-amino-6-methoxy-9H-purin-9-yl) cyclobutyl)methyl bis (pivaloyloxymethyl) phosphate, methyl (((cis-3-(2-amino-6-methoxy-9H-purin-9-yl) cyclobutyl)methoxy)(4-chloro-2-fluorophenoxy) phosphoryl)-L-alaninate, and methyl (((cis-3-(2-amino-6-methoxy-9H-purin-9-yl) cyclobutyl) methoxy)(3-bromophenoxy) phosphoryl)-L-alaninate; or a salt thereof.

* * * * *

```
SEQUENCE LISTING

Sequence total quantity: 2
SEQ ID NO: 1            moltype = DNA  length = 17
FEATURE                 Location/Qualifiers
misc_feature            1..17
                        note = Synthetic oligonucleotide sequence
source                  1..17
                        mol_type = other DNA
                        organism = synthetic construct
SEQUENCE: 1
gtaaaacgac ggccagt                                                   17

SEQ ID NO: 2            moltype = DNA  length = 70
FEATURE                 Location/Qualifiers
misc_feature            1..70
                        note = Synthetic oligonucleotide sequence
source                  1..70
                        mol_type = other DNA
                        organism = synthetic construct
SEQUENCE: 2
ccggggatcc tctagagtcg acctgcaggc atgcaagctt ggcactggcc gtcgttttac   60
aacgtcgtga                                                           70
```